(12) United States Patent
Avey et al.

(10) Patent No.: US 8,290,795 B2
(45) Date of Patent: Oct. 16, 2012

(54) METHOD FOR USING ENVIRONMENTAL CLASSIFICATION TO ASSIST IN FINANCIAL MANAGEMENT AND SERVICES

(75) Inventors: Donald P. Avey, Ankeny, IA (US); Phillip Lee Bax, Johnston, IA (US); Richard Glenn Brooke, Johnston, IA (US); David S. Ertl, Waukee, IA (US); Joseph K. Gogerty, Algona, IA (US); David J. Harwood, Chatham (CA); Michael J. Lauer, Des Moines, IA (US); Terry Eu Claire Meyer, Urbandale, IA (US); Todd A. Peterson, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 487 days.

(21) Appl. No.: 12/330,710

(22) Filed: Dec. 9, 2008

(65) Prior Publication Data

US 2009/0112637 A1    Apr. 30, 2009

Related U.S. Application Data

(62) Division of application No. 11/423,652, filed on Jun. 12, 2006, now Pat. No. 8,046,280.

(60) Provisional application No. 60/689,716, filed on Jun. 10, 2005.

(51) Int. Cl.
    *G06Q 40/00* (2012.01)
(52) U.S. Cl. .......................................................... 705/4
(58) Field of Classification Search ................. 705/4
    See application file for complete search history.

(56) References Cited

U.S. PATENT DOCUMENTS

| | | |
|---|---|---|
| 2,446,509 A | 8/1948 | Fischer |
| 3,727,345 A | 4/1973 | Smith |
| 4,159,596 A | 7/1979 | Downing |
| 4,291,082 A | 9/1981 | Stall |
| 4,554,761 A | 11/1985 | Tell |
| 5,492,547 A | 2/1996 | Johnson |
| 5,538,880 A | 7/1996 | Lundquist et al. |

(Continued)

FOREIGN PATENT DOCUMENTS

| | | |
|---|---|---|
| WO | WO 97/09696 A1 | 3/1997 |
| WO | WO 01/33505 A2 | 5/2001 |

OTHER PUBLICATIONS

PCT/US 06/22917, Pioneer Hi-Bred International, Inc., International Search Report, Jun. 12, 2006, 3 pages.

(Continued)

*Primary Examiner* — James Vezeris
(74) *Attorney, Agent, or Firm* — Woodcock Washburn LLP

(57) ABSTRACT

Managing risks of crop production can be performed by understanding the relative performance of different agricultural inputs under the same or similar environmental conditions. In addition, managing of crop production risks can be performed by understanding variations in the performance of the same agricultural inputs over a range of environmental conditions. By being able to describe and understand these variations in performance, decisions can be made which are consistent with overall business and/or production objectives and limit risk associated with variations in environmental conditions. In addition to producers there are other stakeholders in the crop production process, such as financial institutions, insurance providers, users of crops produced, and input suppliers. These and other stakeholders can provide financial incentives to producers for managing crop production risks through use of environmental classification and/or genotype-by-environment information.

3 Claims, 19 Drawing Sheets

U.S. PATENT DOCUMENTS

| | | | |
|---|---|---|---|
| 5,689,914 | A | 11/1997 | Greaves et al. |
| 5,884,244 | A | 3/1999 | Phaal |
| 5,897,619 | A * | 4/1999 | Hargrove et al. ............... 705/4 |
| 5,978,723 | A | 11/1999 | Hale et al. |
| 5,981,832 | A | 11/1999 | Johnson |
| 6,008,756 | A | 12/1999 | Boerhave et al. |
| 6,100,093 | A | 8/2000 | Van Kooten et al. |
| 6,141,904 | A | 11/2000 | Greaves et al. |
| 6,212,824 | B1 | 4/2001 | Orr et al. |
| 6,282,835 | B1 | 9/2001 | Richtsmeier |
| 6,338,040 | B1 | 1/2002 | Buman et al. |
| 6,433,146 | B1 | 8/2002 | Cheryan |
| 6,455,758 | B1 | 9/2002 | Johnson |
| 6,505,146 | B1 | 1/2003 | Blackmer |
| 6,549,852 | B2 * | 4/2003 | Hanson ........................ 702/2 |
| 6,691,135 | B2 | 2/2004 | Pickett et al. |
| 6,778,872 | B2 | 8/2004 | Jorgenson et al. |
| 6,865,556 | B2 | 3/2005 | Penner et al. |
| 6,945,459 | B2 | 9/2005 | Flanagan |
| 6,990,459 | B2 | 1/2006 | Schneider |
| 6,999,877 | B1 | 2/2006 | Dyer et al. |
| 7,039,592 | B1 | 5/2006 | Yegge et al. |
| 7,047,135 | B2 | 5/2006 | Dyer et al. |
| 7,167,797 | B2 | 1/2007 | Faivre et al. |
| 7,184,892 | B1 | 2/2007 | Dyer et al. |
| 7,193,128 | B2 | 3/2007 | Copenhaver et al. |
| 7,321,310 | B2 | 1/2008 | Curkendall et al. |
| 7,844,475 | B1 | 11/2010 | Murphy |
| 8,046,280 | B2 | 10/2011 | Avey et al. |
| 2002/0082982 | A1 | 6/2002 | Mock et al. |
| 2002/0103688 | A1 | 8/2002 | Schneider |
| 2002/0173980 | A1 | 11/2002 | Daggett et al. |
| 2002/0183867 | A1 | 12/2002 | Gupta et al. |
| 2003/0083819 | A1 | 5/2003 | Rooney et al. |
| 2003/0125877 | A1 | 7/2003 | Hanson |
| 2003/0126635 | A1 | 7/2003 | Penner et al. |
| 2003/0129973 | A1 | 7/2003 | Oishi et al. |
| 2003/0229435 | A1 | 12/2003 | Van der Lely |
| 2003/0236724 | A1 | 12/2003 | Baranova et al. |
| 2004/0073556 | A1 | 4/2004 | Wood et al. |
| 2004/0132370 | A1 | 7/2004 | Schroder |
| 2004/0133347 | A1 | 7/2004 | Britt |
| 2004/0210509 | A1 | 10/2004 | Eder |
| 2004/0215556 | A1 | 10/2004 | Merkley et al. |
| 2004/0264762 | A1 | 12/2004 | Mas et al. |
| 2005/0004682 | A1 | 1/2005 | Gaddis et al. |
| 2005/0027572 | A1 | 2/2005 | Goshert |
| 2005/0050796 | A1 | 3/2005 | Wilkin |
| 2005/0096849 | A1 | 5/2005 | Sorrells |
| 2005/0125260 | A1 | 6/2005 | Green et al. |
| 2005/0150160 | A1 | 7/2005 | Norgaard et al. |
| 2005/0153687 | A1 | 7/2005 | Niemenmaa et al. |
| 2005/0153987 | A1 | 7/2005 | Berg et al. |
| 2005/0208925 | A1 | 9/2005 | Panasik et al. |
| 2005/0283314 | A1 | 12/2005 | Hall |
| 2006/0015253 | A1 | 1/2006 | Ochs et al. |
| 2006/0015360 | A1 | 1/2006 | Ochs et al. |
| 2006/0015374 | A1 | 1/2006 | Ochs et al. |
| 2006/0030990 | A1 | 2/2006 | Anderson et al. |
| 2006/0074560 | A1 | 4/2006 | Dyer et al. |
| 2006/0106539 | A1 | 5/2006 | Choate et al. |
| 2006/0282295 | A1 | 12/2006 | McComb et al. |
| 2006/0282467 | A1 | 12/2006 | Peterson et al. |
| 2006/0287896 | A1 | 12/2006 | McComb et al. |
| 2007/0174095 | A1 | 7/2007 | McComb et al. |
| 2008/0040165 | A1 | 2/2008 | Anderson et al. |
| 2010/0306012 | A1 | 12/2010 | Zyskowski et al. |

OTHER PUBLICATIONS

Cooper, M. et al., "Integrating tools and generating information for efficient plant breeding: Past, Present and Future", International Symposium on Plant Breeding, Aug. 17-22, 2003.

"Classification of Maize Environments using Crop Simulation and GIS", Pioneer Crop Genetics Research, presented at CIMMYT, Apr. 15-16, 2003.

Loffler, Carlos M., et al., "Characterization of Maize Environments using Crop Simulation and GIS", 4th International Crop Science Congress, Sep. 2004.

Loffler, Carlos M., "Characterization of Maize Environments Using Crop Simulation and GIS", Presented at University of Florida, Sep. 9, 2004.

Loffler, Carlos M., "Classification of Maize Environments using Crop Simulation and Geographic Information Systems", ASTA Annual Corn and Sorghum Research Conference, Dec. 9, 2004.

Loffler, Carlos M., "New Methodologies for Managing Genotype by Environment Interaction", VIII Congreso Nacional de Maiz, Rosario, Argentina, Nov. 16-18. 2005.

Wei, Jun et al., "Impact of Genotype and Environment on Historical Corn Production in the USA". ASA Annual Meeting, Las Vegas, Nevada, Nov. 2003.

"Self Pollination Auto Fecondation", Sales page, OSMOLUX: Emerging Technologies—No Contamination, No Rotting, Jun. 18, 2003, 1 page.

"Assessing the Composition of Dairy Products and Grain by Near Infrared", Chemometrics Applications Overview, InfoMetrix, Inc., Oct. 1996, 4 pages.

"Fieldstar Advanced Precision Farming System", AGCO Limited, 2001, 16 pages.

"Fieldstar-Maximizing Farm Profitability and Improving Environmental Practices", AGCO Corporation, retrieved from website archived Jun. 30, 2004, 2 pages.

Davis, "Corn Milling, Processing and Generation of Co-Products", Minnesota Nutrition Conference, Minnesota Corn Growers Association, Sep. 11, 2001, 7 pages.

Doehlert et al., "Genotypic and Environmental Effects on Grain Yield and Quality of Oat Grown in North Dakota", Crop Science, Jul.-Aug. 2001, 41, 1066-1072.

Haefele et al., "Selection and Optimization of Corn Hybrids for Fuel Ethanol Production", American Seed Trade Association's Proceedings of the 59th Annual Corn and Sorghum Research Conference, Dec. 2004, 21 pages.

Hume, "A Possible New Method for the Control of Pollen in Corn", Journal of the American Society of Agronomy, Mar. 1941, 33(3), 265-266.

Lawton, "Buy into bundling benefits", Farm Industry News, Mar. 15, 2002, 4 pages.

Mazur et al., "Gene Discovery and Product Development for Grain Quality Traits", Science, Jul. 16, 1999, 285(5426), 372-374.

PCT Application No. PCT/US2007/88510 : International Search Report of the International Searching Authority, Jun. 10, 2008, 1 page.

Semchenko et al., "The Effect of Breeding on Alometry and Phenotypic Plasticity in Four Varieties of Oat", Field Crops Research, Sep. 14, 2005, 93(2-3), 33 pages.

Thomison, "Cultural Practices for Optimizing Maize Seed Yield and Quality in Production Fields", M.B. McDonald and S. Contreras (ed.) Proceedings International Seed Seminar: Trade, Production and Technology, Oct. 15-16, 2002, 49-55.

Tiffany et al., "Factors Associated with Success of Fuel Ethanol Products", Staff Paper P03-7, Department of Applied Economics, College of Agricultural, Food, and Environmental Sciences, University of Minnesota, Aug. 2003, 62 pages.

Wehling et al., "Prediction of Corn Dry-Milling Quality by Near-Infrared Spectroscopy", Cereal Chemistry, Jun. 1996, 73(5), 543-546.

"Quality Characteristics of Grains". Retrieved from http://www.fao.org/docrep/T1838E/T18380h.htm, archived Dec. 14, 2001, 2 pages.

"Grain Grading Standards in Feed Manufacturing", Kansas State University Agricultural Experiment Station and Cooperative Extension Service. Department of Grain Science and Industry. MF-2034, Jan. 1997, 12 pages.

"Grain Inspection Handbook. Book II, Chapter 2: Barley", US Department of Agriculture. Grain Inspection, Packers and Stockyards Administration. Federal Grain Inspection Service, Aug. 9, 2004, 35 pages.

Morris, C. F.; "Southern Idaho Dryland Winter Wheat Production Guide: Grain Quality-Idaho Wheat Production Guide", University of Idaho College of Agricultural and Life Sciences, Jan. 2004, pp. 6-9.

* cited by examiner

| Product | Acres | Risk Assessment | Crop Revenue Assurance |
|---|---|---|---|
| Hybrid1 | Acres1 | X prob | $1 |
| Hybrid2 | Acres2 | Y prob | $2 |
| Hybrid3 | Acres3 | Z prob | $3 |

FIG. 11

Site Specific Information

Location _____ —172

Environment and Production Information

- Maturity Days [▼] —176
- Input Traits [▼] —178
- Output Traits [▼] —180
- Seed Treatment [▼] —182
- No Till ☐ —174
- Planting Population _____ —184
- Nitrogen Utilization [▼] —186
- Drought Frequency _____ —187

[Select Hybrid]

| Hybrid Name | Hybrid Rank | Risk Assessment |
|---|---|---|
| Hybrid1 | 99% | 0.075 prob |
| Hybrid2 | 89% | 0.15 prob |

Site Specific Information

Location: _____ (172)

Soil Type: _____ ▼ (174)

Acres: _____ (202)

[Import Precision Farming Data] (204)

[Import Environment Frequency Data] (205)

[Set Production Practices] —206

[Set Environmental Assumptions] —208

[Set Risk Levels] —210

Max Number of Hybrids: _____ ▼ —212

Portfolio Results

| Product | Acres | Hybrid Rank | Risk Assessment | Revenue Assurance |
|---------|-------|-------------|-----------------|-------------------|
| Hybrid1 | Acres1 | 1 (97%) | .15 prob | $ |
| Hybrid2 | Acres2 | 3 (87%) | .20 prob | $ |
| Hybrid3 | Acres3 | 2 (92%) | .03 prob | $ |

214, 216, 217, 218, 219

[Generate Precision Farming Information] (220)

METHOD FOR USING ENVIRONMENTAL CLASSIFICATION TO ASSIST IN FINANCIAL MANAGEMENT AND SERVICES

CROSS-REFERENCE TO RELATED APPLICATIONS

This application is a Divisional Application of U.S. Ser. No. 11/423,652 filed Jun. 12, 2006, which also claims priority under 35 U.S.C. §119 of a provisional application Ser. No. 60/689,716 filed Jun. 10, 2005, hereby incorporated by reference in their entirety.

BACKGROUND OF THE INVENTION

The present invention provides for computer-implemented methods and related methods which tie financial management and/or financial services to the use of environmental classification in making agricultural production decisions.

Agricultural production has attendant uncertainties and risks. Managing such risks are important not only to the success of the production operation, but also to related industries. These include, without limitation, banks or other financial institution that provide financing for producers; input suppliers, such as, but not limited to seed suppliers, chemical suppliers, equipment suppliers, and others; purchasers or users of the produced crops, including livestock producers, ethanol or bio-diesel producers, and food manufacturers. Thus, there are many potential stakeholders in agricultural production.

What is needed is a method for product selection that is useful in characterizing relative performance of different agricultural inputs under different conditions so that risk can be managed in a way that can assist in making financial management decisions, including not only decisions made by producers, but also decisions made by other stakeholders.

SUMMARY OF THE INVENTION

Therefore it is a primary object, feature, or advantage of the present invention to improve over the state of the art.

Another object, feature, or advantage of the present invention is to provide a method to assist stakeholders in agricultural production in managing financial risks associated with crop production.

Yet another object, feature, or advantage of the present invention is to assist stakeholders in agricultural production and others in understanding relative performance of different agricultural inputs, including seed products, under the same or similar environmental conditions.

A still further object, feature, or advantage of the present invention is to assist stakeholders in agricultural production and others in understanding relative performance of an agricultural input, such as a seed product, under a range of environmental conditions.

Another objective, feature, or advantage of the present invention is to assist producers in selecting the best seed product for a particular location.

Yet another object, feature, or advantage of the present invention is to provide additional incentives to producers for selecting seeds products for a particular location with a greater likelihood of desired performance.

According to one aspect of the present invention a method for reducing risk associated with making a financial decision related to crop production is provided. The method includes identifying a land base for the crop production, classifying the land base to provide an environmental classification, receiving an indication of the seed product selected for production, and evaluating relative risk associated with the production of different genotypes of seed products by comparing predicted relative performance of a plurality of seed products, each seed product having a genotype. The predicted relative performance is at least partially based on predicted genotype by environment interactions between each seed product and the environmental classification of the land base. The plurality of seed products includes the seed product selected for production. The method further includes providing a financial decision at least partially based on the risk associated with the use the seed product selected for production relative to one or more other seed products within the plurality of seed products. The environmental classification may be based on data collected from a plurality of locations over a number of years to provide information regarding the frequency of particular environmental classifications at various locations. Thus, experience with a genotype over a variety of different environments assists in determining and applying the environmental classifications.

The financial decision may of various types or kinds. For example, the financial decision may be a determination of whether to finance the crop production, whether to contract for purchasing crops resulting from the crop production, or a determination of terms of financing for the crop production. The performance may be measured in various ways, including yield, content (such as, but not limited to protein content, oil content, starch content, moisture content), or quality. The performance may be related to the end use of the crop, such as use in ethanol production, bio-diesel production, livestock use, or food manufacturing.

According to another aspect of the present invention, a method for providing financing is provided. The method includes evaluating the use of agricultural inputs associated with a producer according to an environmental classification system. Each of the agricultural inputs are classified according to the environmental classification system. A land base associated with the producer is also classified according to the environmental classification system. A financing decision associated with the producer is made based on the results form the step of evaluating. The financing decision may of numerous types. For example, without limitation, the financing decision can be a decision as to whether or not to finance the producer or a decision regarding the terms of financing. These decisions are preferably related to an assessment of the production risks using the environmental classification system.

According to another aspect of the present invention, a method for providing a financial incentive for use of an environmental classification system in making production management decisions is provided. The method includes providing to a producer recommendations of agricultural inputs to use. The recommendations are based, at least in part, on environmental classification associated with the agricultural inputs and an environmental classification associated with a land base of the producer. The method further provides for giving the producer a financial incentive to select agricultural inputs based on the recommendations. The financial incentives may include a reduced purchase price for one or more of the agricultural inputs, preferred financing terms, a reduced interest rate on financing, or other types of financial incentives.

According to another aspect of the present invention, a method for providing a financial incentive for use of genotype by environment information in selecting a seed product is provided. The method includes providing to a producer a recommendation of one or more seed products to use to produce crop on a land base of the producer. The recommendation based in whole or in part on relative performance of seed products under environmental conditions associated with the land base of the producer and interactions between the genotype of each of the plurality of seed products and the environmental conditions. The method further includes giving the producer a financial incentive to accept the recommendation. The financial incentive may be of various kinds or types. The financial incentive may include a reduced purchase price for one or more of the agricultural inputs, preferred financing terms, a reduced interest rate on financing, and/or other types of financial incentives.

According to another aspect of the present invention, a method for providing a crop and/or revenue insurance policy to a producer is provided. The method includes receiving an evaluation of the use of agricultural inputs associated with a producer according to an environmental classification system wherein each of the agricultural inputs being classified according to the environmental classification system and a land base associated with the producer being classified according to the environmental classification system. The method further includes determining one or more terms of the crop insurance policy at least partially based on the step of evaluating use of agricultural inputs and providing the crop insurance policy to the producer. The environmental classification system is preferably at least partially based on genotype by environment interactions. The terms of the crop or revenue insurance policy may take into account the risk associated with particular product decisions or with the use of particular agricultural inputs. The terms of the crop or revenue insurance may be based on the history of a producer or decisions for the upcoming or current crop.

BRIEF DESCRIPTION OF THE FIGURES

FIG. 11 is a screen display showing a product portfolio according to one embodiment of the present invention.

FIG. 12 is a screen display for one embodiment of an application of the present invention.

FIG. 13 is a screen display for one embodiment of an application of the present invention.

DETAILED DESCRIPTION OF THE PREFERRED EMBODIMENT

Figure 1:
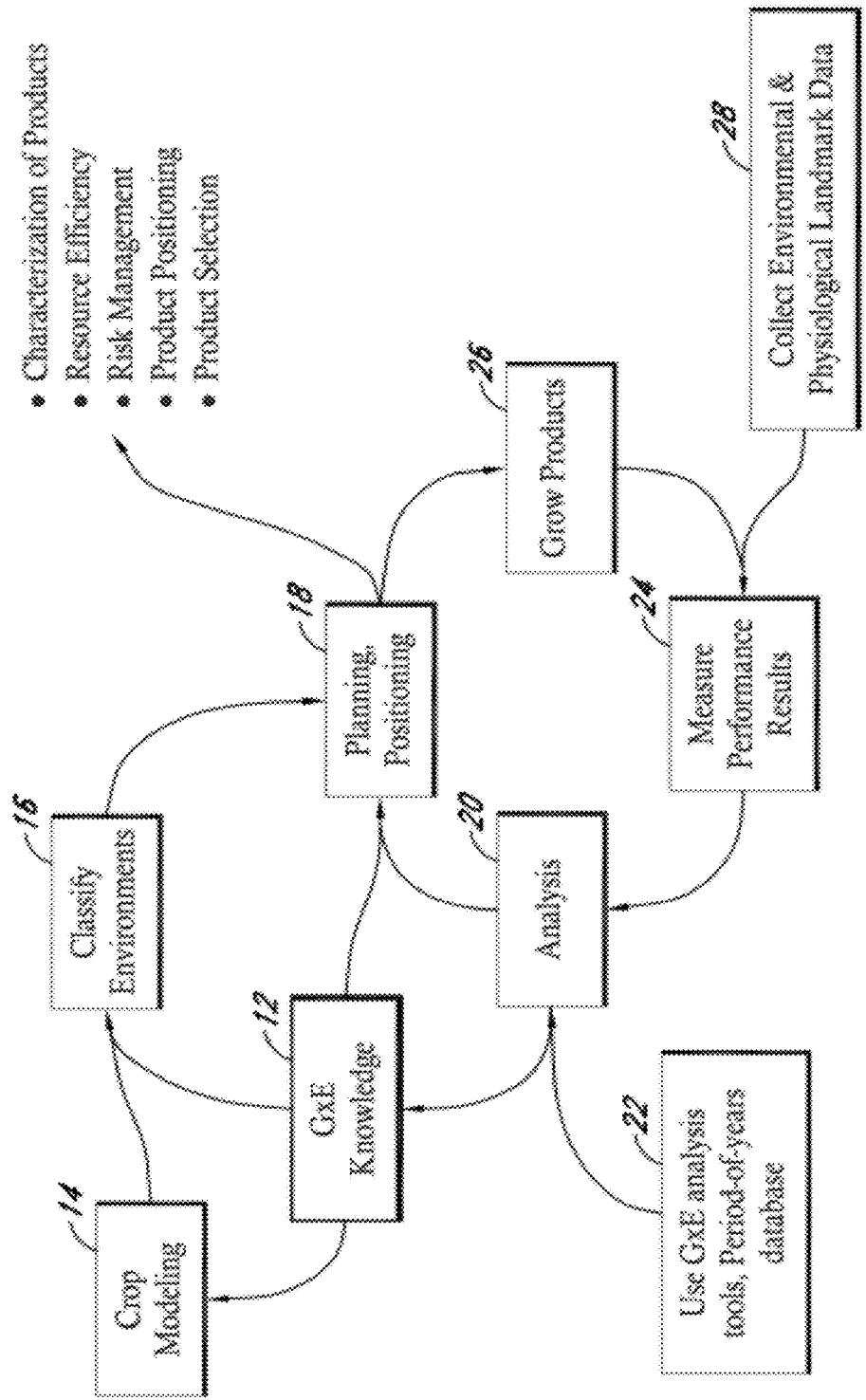
FIG. 1 is a flow diagram illustrating one process for determining genotype-by-environment interactions and using that information in categorizing land bases into different environmental classifications.

The present invention provides methods which tie financial management and/or financial services to the use of environmental classification in making production decisions. The present invention uses environmental classification and/or an understanding of genotype-by-environment interactions to manage production risks and recognizes that financial risks can be better managed where the production risks are managed. Thus, financial decisions can be made, or financial incentives provided based upon knowledge of genotype-by-environmental classifications and/or environmental classification.

Managing risks of crop production can be performed by understanding the relative performance of different agricultural inputs, including different seed products, under the same or similarly defined environmental conditions. In addition, managing of crop production risks can be performed by understanding variations in the performance of the same agricultural input over a range of environmental conditions. By being able to describe and understand the reasons behind these variations in performance, decisions can be made which are consistent with overall business and/or production objectives and limit risk associated with variations in environmental conditions. These decisions can include what seed products or combination of seed products to plant, where to plant different seed products, what other agricultural inputs to use, and what crop management practices to apply.

One method to manage risks associated with crop production uses knowledge of genotype-by-environment interactions to assist a producer or other customer in selecting seed products to plant in one or more fields. A "genotype" is generally defined as a cultivar, genetically homogenous (lines, clones), a hybrid of two or more parents, or heterogeneous (open-pollinated populations). An "environment" is generally defined as a set of conditions, such as climatic conditions, soil conditions, biotic factors (such as, without limitation, pests and diseases) and/or other conditions that impact genotype productivity. "Management" as used in this context generally refers to production management decisions, such as, but not limited to crop production practices. In addition, the present invention allows for the use of environmental characterizations to assist in describing genotype-by-environment interactions. It is to be understood that the term "genotype-by-environment" (G×E) is to encompass what is sometimes known or referred to as "genotype-by-environment-by management" (G×E×M) as the environment associated with a plant may include management practices which affect the environment (for example, irrigation may be considered a management practice, but use of irrigation affects the growing environment).

Following, is an exemplary description regarding the use of G×E interactions and environmental classification. Next, an exemplary description is provided regarding how a producer or other stakeholder uses this information in order to make management decisions. Then, the ways in which financial management and financial incentives can be tied to knowledge of G×E interactions and/or environmental classification is discussed.

G×E and Environmental Classification

Genetic manipulation alone does not ensure that a plant will perform well in a specific environment or for that matter a wide range of environments year after year. In other words, there is no one genotype that is likely to perform best in all environments or under all management practices. The performance or phenotype results from an interaction between the plant's genotype and the environment and the management practices used.

It is to be understood that there are some inherent difficulties in understanding such interactions. An environment at a given location changes over the years making multi-environment trials (METs) performed in the same location limited as to inferences about future crop performance. Furthermore, inferences about a crop's future performance in different locations depend on whether the target population of environments (TPEs) is well sampled since the environment varies between different locations in one year.

To assist in analyzing such interactions, the present invention preferably uses environmental classification techniques. The environmental classification techniques are used, preferably with a large set of data to relate performance of different genotypes to different environments. Environmental classification is then used when selecting the best seed products for a particular land base. Thus, for example, a producer can use environmental classification to select the best seed products for their land base based on the expected environmental conditions. Alternatively, the producer may diversify and select a combination of seed products based on a range of expected environmental conditions to thereby manage risks associated with environmental variability. Of course, environmental classification can be used by not just producers but others having interest in agricultural production.

FIG. 1 provides an overview of one G×E paradigm where G×E knowledge 12 is used in planning and positioning 18. G×E knowledge 12 can be applied to crop modeling 14. Crop modeling 14 and G×E knowledge 12 may either alone or together be used to classify environments. The G×E knowledge 12 and classified environments may be used in facilitating the positioning and/or planning 18 strategies, such as characterization of products, resource efficiency, risk management, product positions, and product selection.

Subsequent to positioning and planning, the producer will grow the selected products 26 and measure the performance results 24. The producer may also collect environmental and physiological landmark data 28 and in conjunction with performance results 24 use it in analysis 20. Analysis of environmental and physiological landmark data 28 and performance results 24 may undergo analysis 20 using G×E analysis tools or period-of-years database 22. In addition, the output of records of product use and production practices can assist in decision making and regulatory compliance.

Building an Environmental Classification System

The effectiveness of a product evaluation system for genotype performance largely depends on the genetic correlation between multi-environment trials (MET) and the target population of environments (TPE) (Comstock, R. E. 1977. 'Proceedings of the International Conference on Quantitative Genetics, Aug. 16-21, 1976' pp. 705-18. Iowa State University Press. Ames, USA.). For example, previous characterizations of maize environments relied mainly on climatic and soil data (e.g. Hartkamp, A. D., J. W. White, A. Rodriguez Aguilar, M. Bänziger, G. Srinivasan, G. Granados, and J. Crossa. 2000. Maize Production Environments Revisited: A GIS-based Approach. Mexico, D. F. CIMMYT.; Pollak, L. M., and J. D. Corbett. 1993. Agron. J. 85:1133-1139; Runge, E. C. A. 1968. Agron. J. 60:503-507). While useful to describe environmental variables affecting crop productivity, these efforts did not quantify the impact of these variables on the genetic correlations among testing sites. Consequently, plant breeders have more extensively used characterizations of environments based on similarity of product discrimination in product evaluation trials (e.g. Cooper, M., D. E. Byth, and I. H. DeLacy. 1993. Field Crops Res. 35:63-74). However, these efforts frequently fail to provide a long-term assessment of the target population of environments (TPE), mainly due to the cost and impracticality of collecting empirical performance data for widespread and long-term studies.

The present invention provides a modern approach of product evaluation where a TPE is described. The description of a TPE includes classifying the land base into an environmental class and assessing the frequency of occurrence of the range of environments experienced at a given location. The present inventors contemplate that areas of adaption (AOA) could also be evaluated. As used herein AOA refers to a location with the environmental conditions that would be well suited for a crop or specific genotype. Area of adaption is based on a number of factors, including, but not limited to, days to maturity, insect resistance, disease resistance, and drought resistance. Area of adaptability does not indicate that the crop will grow in every location or every growing season within the area of adaption or that it will not grow outside the area. Rather it defines a generally higher probability of success for a crop or genotype within as opposed to outside that area of adaptation.

The environmental information collected may be used to develop an environmental database for research seed product locations, or grower commodity production locations. Initially, multiple environment trials are performed by planting different genotypes available from a variety of sources, e.g. germplasm, inbreds, hybrids, varieties in multiple environments. These trials aid the determination of whether the TPEs are homogenous or should be categorized into different environmental classifications. The performance data of these genotypes and environmental and/or physiological landmark data from the MET are collected and entered into a data set. For example, performance data collected for a genotype of corn may include, but is not limited to, any of the following: yield, grain moisture, relative maturity, stalk lodging, stand establishment, emergence, midsilk, test weight, protein, oil, and starch. Yield refers to bushels of grain per acre. Grain moisture refers to a moisture determination made from each plot at harvest time, using an instrument such as an electrical conductance moisture meter. Stalk lodging refers to the determination of the number of broken stalks in each plot prior to harvest. Stand establishment refers to the differences between the desired planting rate for each hybrid and the final stand. Emergence refers to an emergence count made on each plot after plant emergence where emergence percentage may be computed based on the number of plants and the number of kernels planted. The mid silk date is the Julian day of the year in which 50% of the plants show silks at one site in a region. The test weights are typically reported as pounds per bushel on grain samples at field moisture. Protein, oil and starch are typically reported as a percent protein, oil, and starch content at a designated percent grain moisture on dried samples using standard methods, for example, a near infrared transmittance whole grain analyzer.

One skilled in the art would be familiar with performance data collected for other crops, for example, soybeans, wheat, sunflowers, canola, rice and cotton. Performance data for soybeans include, without limitation, relative maturity, soybean cyst nematode tolerance/resistance, plant height, lodging score, seed size, protein and oil percentage, Phytophthora resistance genes, Phytophthora partial resistance, Sclerotinia rating, and yield. Relative maturity refers to a determination that is designed to account for factors, such as soybean variety, planting date, weather, latitude and disease that affect maturity date and number of days from planting to maturity. Plant height refers to a determination of the soybean plant's height, usually determined prior to harvest. Lodging, traditionally, the vertical orientation of the plant, i.e. the degree to which the plant is erect. The lodging of a soybean plant is traditionally rated by researchers using a scale of 1 to 9 as follows: 1.0=almost all plants erect, 3.0=either all plants leaning slightly, or a few plants down, 5.0=either all plants leaning moderately (45 degree angle), or 25-50% down, 7.0=either all plants leaning considerably, or 50-80% down, 9.0 all plants prostrate. The seed size of a soybean plant typically refers to thousands of seeds per pound. Protein and oil percentage analysis may be determined using near infrared transmittance technology and reported at 13% moisture. Phytophthora resistance genes may be determined using a hypocotyl inoculation test with several races of Phytophthora to determine the presence or absence of a particular Rps gene in a soybean plant. Soybeans may also be evaluated for phytophthora partial resistance using a ratings system, where ratings of 3.0 to 3.9 are considered high levels of partial resistance, ratings of 4.0 to 5.9 are considered moderate, ratings over 6.0 indicate very little partial resistance or protection against Phytophthora. Soybeans may also be evaluated for partial resistance to Sclerotinia. Yield refers to bushels per acre at 13 percent moisture.

Typical performance data for wheat includes, without limitation, test weight, protein percent, seed size, percent lodging, plant height, heading date, powdery mildew, leaf blotch complex (LBC), *Fusarium* head scab (FHS), flour yield, and flour softness. Test weight refers to a determination of pounds/ bushell using harvest grain moisture. Seed size refers to thousands of harvested seeds per pound. Percent lodging as described previously refers to a rating system used to estimate the percent of plants that are not erect or lean more than 45 degrees from vertical. Plant height refers to the distance from the soil surface to the top of the heads. Heading date refers to the average calendar day of the year on which 50 percent of the heads are completely emerged. Wheat infected with powdery mildew (PM) may be determined using a scale system where each plot is rated based on a 0 to 10 scale where: 0=0 to trace % leaf area covered; 1=leaf 4 with trace –50%; 2=leaf 3 with 1-5%; 3 leaf 3 with 5-15%; 4=leaf 3 with >15%; 5=leaf 2 with 1-5%; 6=leaf 2 with 5-15%; 7=leaf 2 with >15%; 8=leaf 1 with 1-5%; 9=leaf 1 with 5-15%; and 10=leaf 1 with >15% leaf area covered (leaf 1=flag leaf). This scale takes into account the percentage leaf area affected and the progress of the disease upward on the plants. Leaf blotch complex (LBC) caused by *Stagonospora nodorum, Pyrenophora triticirepentis* and *Bipolaris sorokiniana* for example may be determined when most varieties are in the soft dough growth stage and rated based on the percentage of flag leaf area covered by leaf blotches. *Fusarium* head scab (FHS) caused by *Fusarium graminearum* for example may be determined when plants are in the late milk to soft dough growth stage and each plot is rated based on a disease severity estimate as the average percentage of spikelets affected per head. Flour yield refers to the percent flour yield from milled whole grain. Flour softness refers to the percent of fine-granular milled flour. Values higher than approximately 50 indicate kernel textures that are appropriate for soft wheat. Generally, high values are more desirable for milling and baking.

Typical performance data for sunflower includes, without limitation, resistance to aphids, neck breakage, brittle snap, stalk breakage, resistance to downy mildew (*Plasmopara halstedii*), height of the head at harvest, seed moisture, head shape, hullability, resistance to the sunflower midge, *Contarinia schulzi*, percentage of oil content, seed size, yield, seedling vigor, and test weight. Resistance to aphids refers to a visual ratings system indicating resistance to aphids based on a scale of 1-9 where higher scores indicate higher levels of resistance. Neck breakage refers a visual ratings system indicating the level of neck breakage, typically on a scale from 1 to 9 where the higher the score signifies that less breakage occurs. Brittle snap refers to a visual rating system indicating the amount of brittle snap (stalk breakage) that typically occurs in the early season due to high winds. The ratings system is based on a scale, usually ranging from 1-9, with a higher score denoting the occurrence of less breakage. A sunflower's resistance to Downy Mildew (*Plasmopara halstedii*) may be determined using a visual ratings scaled system with 9 being the highest and 1 the lowest. A higher score indicates greater resistance. Height of the head at harvest refers to the height of the head at harvest, measured in decimeters. Seed moisture refers to a determination of seed moisture taken at harvest time, usually measured as a percentage of moisture to seed weight. Head shape of a sunflower is measured visually using a scale system where each plot is rated based on a 1 to 9 scale where: 1=closed "midge" ball; 2 trumpet; 3=clam; 4=concave; 5=cone; 6=reflex; 7=distorted; 8=convex; 9 flat. Hullability refers to the ability of a hulling machine to remove seed hulls from the kernel, typically measured on a 1-9 scale where a higher score reflects better hullability. Resistance to the sunflower midge, *Contarinia schulzi*, is determined based on head deformation which is rated on a 1-9 scale where: 9=no head deformation (fully resistant), 5=moderate head deformation, 1=severe head deformation (fully susceptible). The percentage of oil content from the harvested grain is measured and adjusted to a 10% moisture level. The oil content of a sunflower seed may be measured for various components, including palmitic acid, stearic acid, oleic acid, and linoleic acid, using a gas chromatograph. Seed size refers to the percentage of grain that passes over a certain size screen, usually "size 13." Seedling vigor refers to the early growth of a seedling and is often times measured via a visual ratings system, from 1-9, with higher scores indicate more seedling vigor. Yield is measured as quintals per hectare, while test weight of seed is measured as kilograms per hectoliter.

Typical performance data for canola includes, without limitation, yield, oil content, beginning bloom date, maturity date, plant height, lodging, seed shatter, green seed percentage, winter survival, and disease resistance. Yield refers to pounds per acre at 8.5% moisture. Oil content is a determination of the typical percentage by weight oil present in the mature whole dried seeds. Beginning bloom date refers to the date at which at least one flower is on the plant. If a flower is showing on half the plants, then canola field is in 50% bloom. Maturity date refers to the number of days observed from planting to maturity, with maturity referring to the plant stage when pods with seed color change, occurring from green to brown or black, on the bottom third of the pod bearing area of the main stem. Plant height refers to the overall plant height at the end of flowering. The concept of measuring lodging using a scale of 1 (weak) to 9 (strong) is as previously described. Seed shatter refers to a resistance to silique shattering at canola seed maturity and is expressed on a scale of 1 (poor) to 9 (excellent). Winter survival refers to the ability to withstand winter temperatures at a typical growing area. Winter survival is evaluated and is expressed on a scale of 1 to 5, with 1 being poor and 5 being excellent. Disease resistance is evaluated and expressed on a scale of 0 to 5 where: 0=highly resistant, 5=highly susceptible. The Western Canadian Canola/Rapeseed Recommending Committee (WCC/RRC) blackleg classification is based on percent severity index described as follows: 0-30%=Resistant, 30%-50%=Moderately Resistant, 50%-70%=Moderately Susceptible, 70%-90%=Susceptible, and >90%=Highly susceptible.

Typical performance data for cotton includes, without limitation, yield, turnout, micronaire, length, fiber strength of cotton and color grade. Yield is measured as pounds per acre. Turnout refers to lint and seed turnout which is calculated as the percentage of lint and seed on a weight basis as a result of ginning the sub sample from each treatment. Micronaire refers to fiber fineness and maturity and are measured using air flow instrument tests in terms of micronaire readings in accordance with established procedures. Fiber length is reported in 1/32 of an inch or decimal equivalents. Fiber strength is measured in grams per tex and represents the force in grams to break a bundle of fibers one tex unit in size. Color grade for cotton takes into consideration the color, fiber color and whiteness of cotton leaves. Color grade may be determined using a two digit scale. The two digit number is an indication of the fiber color and whiteness (i.e. 13, 51, or 84). The first digit can range from 1 to 8 representing overall color with 1 being the best color and 8 representing below grade colors. The second digit represent a fiber whiteness score. This number ranges from 1 to 5, with 1 representing good white color and 5 representing yellow stained. The second number in the overall color grade represents the leaf score and represents leaf content in the sample.

Typical performance data for rice includes, without limitation, yield, kernel length, straw strength, 50% Heading, plant height, and total milling, and total milling. Yield is measured as bushels per acre at 12% moisture. Straw Strength refers to lodging resistance at maturity and is measured using a numerical rating from 1 to 9 where 1=Strong (no lodging); 3=Moderately strong (most plants leaning but no lodging); 5=Intermediate (most plants moderately lodged); 7=Weak (most plants nearly flat); and 9=Very weak (all plants flat). 50% heading refers to the number of days from emergence until 50% of the panicles are visibly emerged from the boot. Plant height is the average distance from the soil surface to the tip of erect panicle. Total milling refers to the total milled rice as a percentage of rough rice. Whole milling refers to rice grains of 3/4 length or more expressed as a percentage of rough rice.

Of course, other types of performance data may be associated with other types of plants, including without limitation, other grains, fruits, vegetables, and flowering plants.

The environmental and physiological landmark data may be historical using historical meteorological information along with soils and other agronomic information or collected using National Oceanic and Atmospheric Association and/or other public or private sources of weather and soil data. Potential environmental and physiological landmark data that may be collected includes but is not limited to wind, drought, temperature, solar radiation, precipitation, soil type, soil temperature, soil pH, planting and harvesting dates, irrigation, tiled area, previous crop, fertilizer including nitrogen, phosphorous, and potassium levels, insecticide, herbicide, and biotic data, for example, insects and disease. The environmental and physiological landmark data may then be analyzed in light of genotype performance data to determine G×E interactions.

Models

Several models for determining G×E interactions exist. Base models group or classify the locations used to test the hybrids, include several variance components, and stratify the hybrids, for example, according to locations among station-year combinations, locations, or other chosen variances. Of course instead of using stations, the locations can be associated with strip trials, on-farm comparisons, or based on information acquired from producers or others.

For example, as shown in Table 1, one base model Year Station (YS) groups the locations by year-stations where a year-station designates a unique site or location by year. Other variances include blocks within locations within year-stations, hybrids, hybrids by year-station divided by the sum of hybrids by locations within year station locations as well as a residual. The YS model is disadvantageous in that a given location's environment will vary over time so that the G×E information gleaned from the model may not be relevant for predicting hybrids that will perform well in the same location next year.

Another model for determining G×E interactions disclosed in Table 1, groups different sites by location. Other variances for the G×E model include blocks within locations, hybrids, hybrids by locations, as well as a residual. However, the G×E model is disadvantageous in that a genotype grown in locations with differing environmental conditions may have similar performance results, complicating the analysis of the specific environmental conditions that play a role in contributing to genotype performance and reducing the certainty of predicting product performance.

Unlike the previous models mentioned, the present inventors contemplate determining G×E interactions using a model referred to herein as Environmental Classification that groups locations by environmental classifications. Thus, variances for this model include locations within environmental classifications, blocks within locations within environmental classifications, hybrids, hybrids by environmental classifications divided by hybrids by locations within environmental classifications and a residual.

TABLE 1

Models for determining G × E interactions

| Model | Year-Station | G × E | Environmental Classification |
|---|---|---|---|
| Variance for location | Location within year-station | Location | Location within environmental classification |

TABLE 1-continued

Models for determining G × E interactions

| Model | Year-Station | G × E | Environmental Classification |
|---|---|---|---|
| Variance for location | blocks within locations within year-station | blocks within locations | blocks within locations within environmental classifications |
| Variance for hybrids | hybrids | hybrids | hybrids |
| Stratifications | hybrid by year-station/hybrids by locations within locations | hybrid by locations | hybrid by environmental classifications/hybrid by locations within environmental classifications |

Burdon has shown that genetic correlation between G×E interactions can be estimated. (Burdon, R. D. 1977. Silvae Genet., 26: 168-175). G×E analysis may be performed in numerous ways. G×E interactions may be analyzed qualitatively, e.g. phenotype plasticity, or quantitatively using, for example, an analysis of variance approach. (Schlichting, C. D. 1986. Annual Review of Ecology and Systematics 17: 667-693). Statistical analysis of whether a G×E interaction is significant and whether environmental changes influence certain traits, such as yield performance, of the genotypes evaluated may be performed using any number of statistical methods including but not limited to, rank correlation, analysis of variances, and stability.

Rank Correlation

Figure 2A:
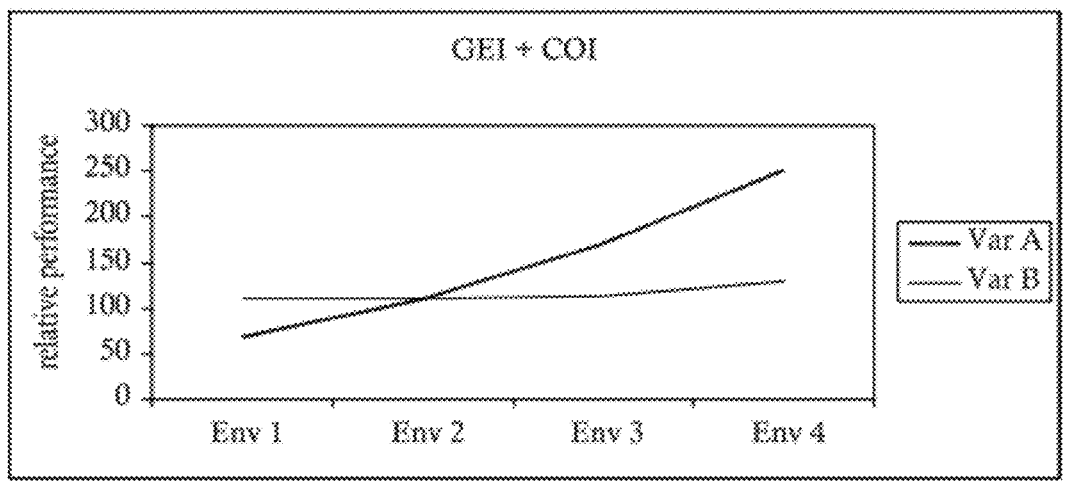
FIG. 2A to FIG. 2C provide an example of genotype by environment interactions and cross-over interactions between two different varieties in four different environmental classes.
Figure 2B:
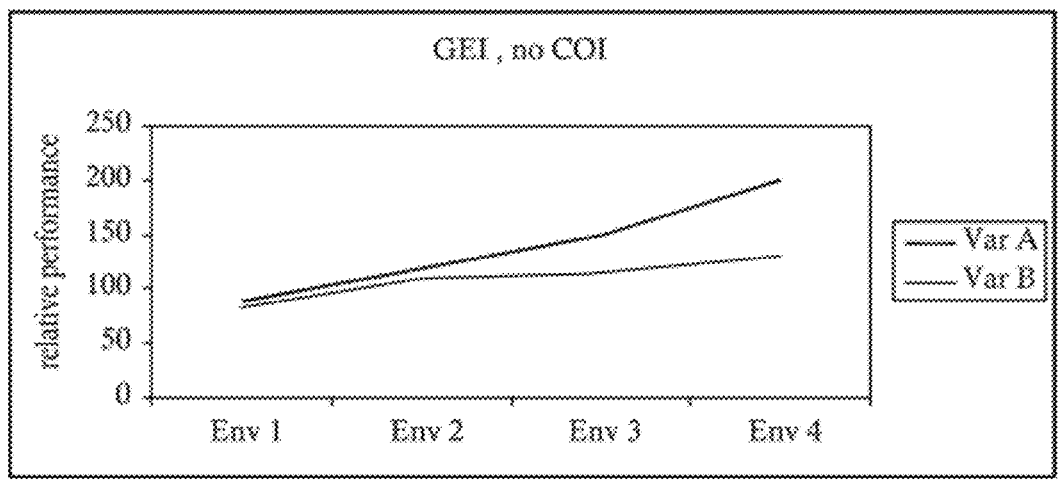
Figure 2C:
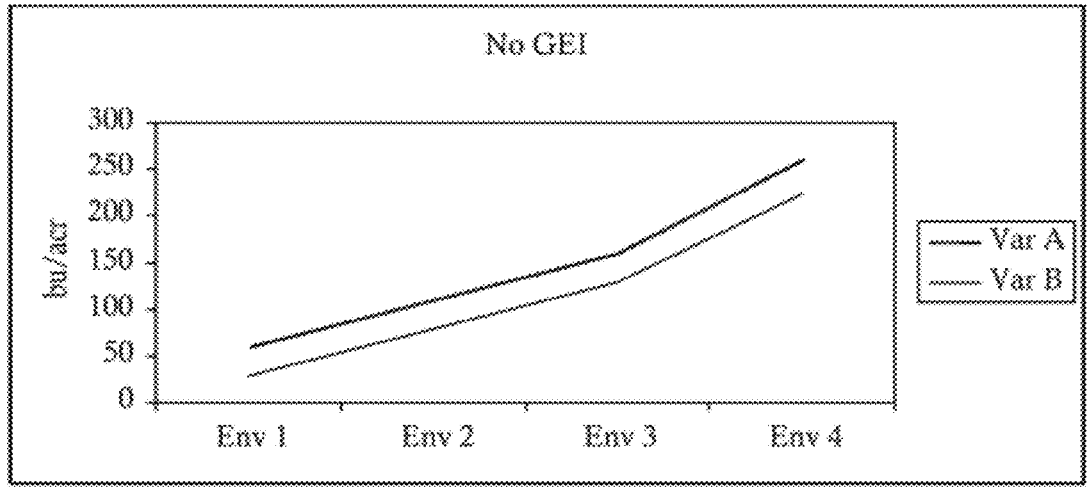

The most basic categorization of G×E interaction is to evaluate G×E interactions by performing a rank correlation according to standardized tests, for example, Spearman. The Spearman rank correlation may be performed to examine the relationships among genotypes in different environments, for example, crossover interactions that occur when two genotypes change in rank order of performance when evaluated in different environments. FIG. 2 illustrates an example of G×E interactions and cross-over interactions (COI) between two different varieties, Var A and Var B, in four different environmental classes, Env 1, Env 2, Env 3 and Env 4. FIG. 2A shows that Var A and Var B out-perform each other in different environments indicating the occurrence of both G×E and COI. FIG. 2B shows that Var A performed better than Var B in each environment, indicating G×E interactions but no COI. In contrast, FIG. 2C shows that Var A and Var B each performed consistently with respect to each other in all four environments, indicating lack of G×E interactions.

Analysis of Variance (ANOVA)

Figure 3:
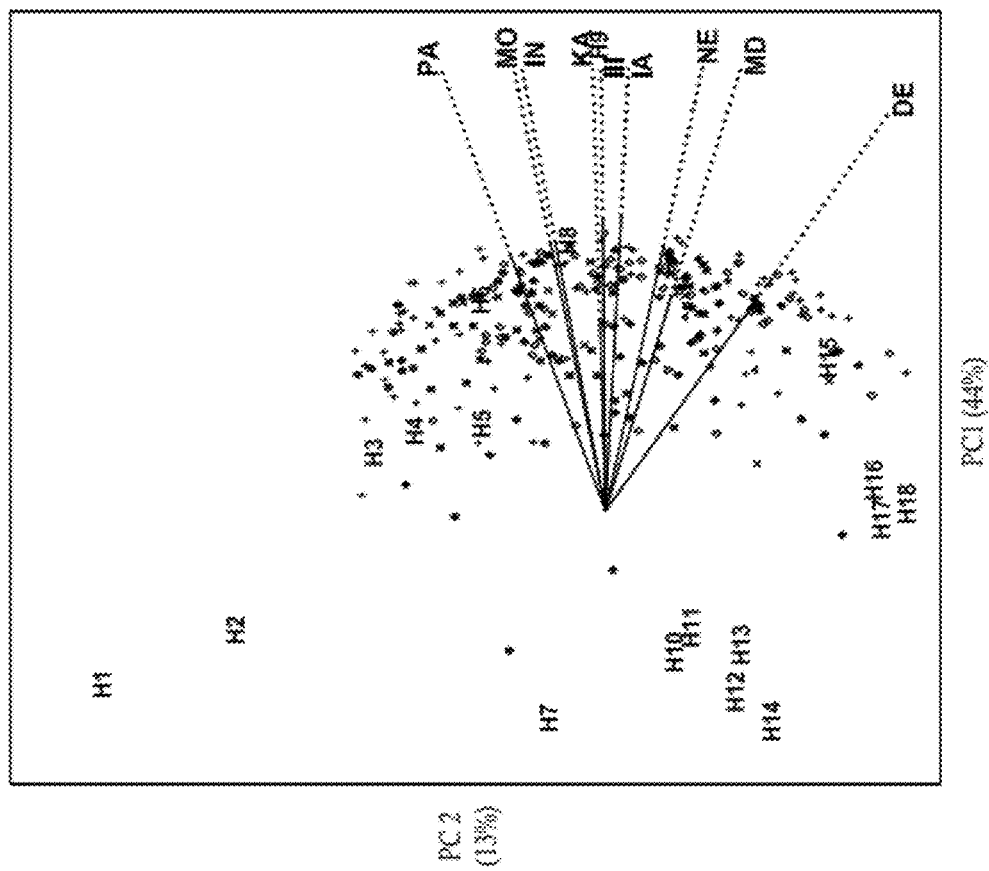
FIG. 3 illustrates environment-standardized GGE biplot of grain yield of 18 maize hybrids (H1-H18) grown in 266 environments over three years stratified by state.
Figure 4:
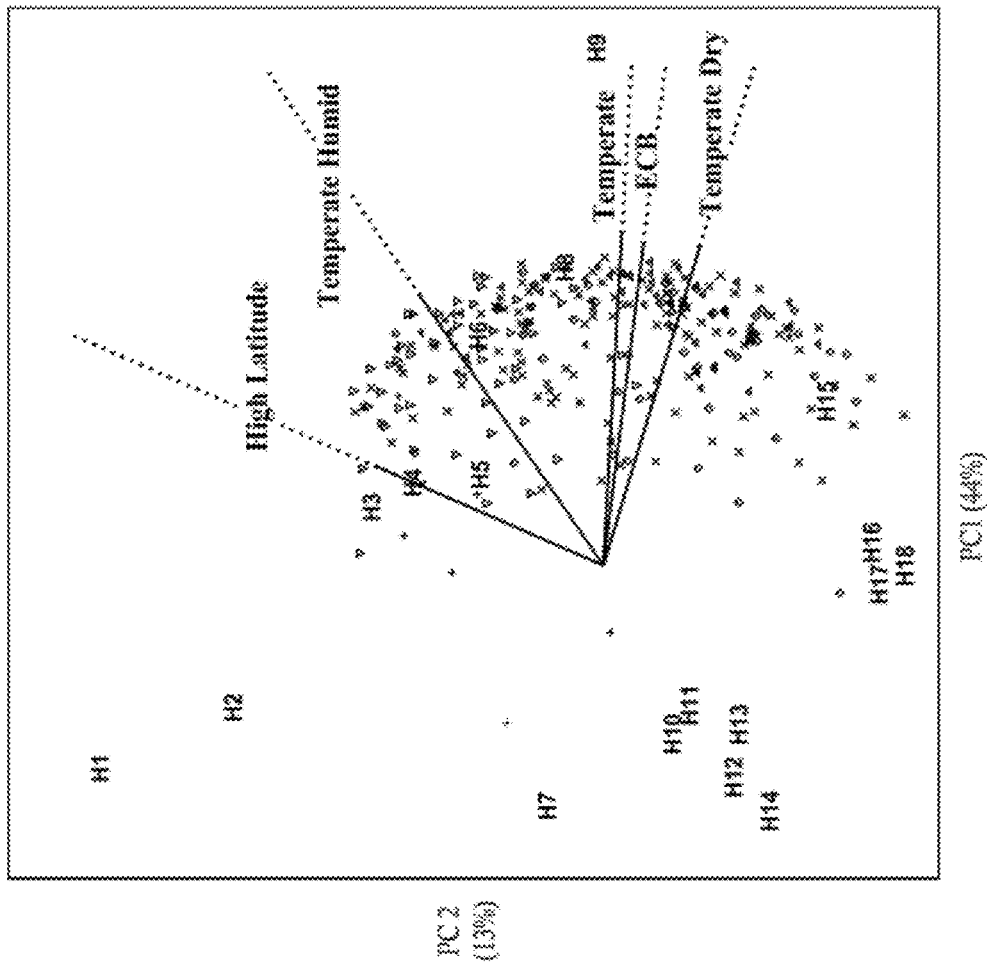
FIG. 4 illustrates environment-standardized GGE biplot of grain yield of 18 maize hybrids (H1-H18) grown in 266 environments over three years stratified by environmental class.

Alternately, G×E interactions may be analyzed using an analysis of variance method (ANOVA) (Steel, R. G. D and J. H. Torrie. 1980. Principles and Procedures of Statistics, 2nd edition) over environments to determine the significance of genotypes, environments and G×E interactions. G×E interactions may also be analyzed using ASREML (Gilmour, A. R., Cullis, B. R., Welham, S. J. and Thompson, R. 2002 ASReml Reference Manual 2nd edition, Release 1.0 NSW Agriculture Biometrical Bulletin 3, NSW Agriculture, Locked Bag, Orange, NSW 2800, Australia.) for the computation of variance components, and the generation of GGE biplots (Cooper, M., and I. H. DeLacy. 1994. Theor. Appl. Genet. 88:561-572; Yan, W. and M. S. Kang. 2003. *GGE Biplot Analysis: A Graphical Tool for Breeders Geneticists, and Agronomists*. CRC Press. Boca Raton, Fla.). FIG. 3 and FIG. 4 illustrate environment-standardized GGE biplot of grain yield of 18 maize hybrids (H1-H18) grown in 266 environments over three years, stratified by state or by environmental class respectively.

Stability

Once certain genotypes are identified that perform well in a target environment they may be analyzed to determine which hybrids are more stable in yield or other metrics using various methods. One method uses a regression of genotypic performance on an environmental index. In general, the environmental index is the deviation of the mean phenotype at environment from the overall mean phenotype of all environments. Thus, the phenotype of an individual genotype with each environment is regressed on the environmental index, as described in Bernardo R. 2002. Quantitative Traits in Plants. Stemma Press, Woodbury, Minn. to generate a slope (b-value) for each genotype/cultivar evaluated. Other methods include the joint regression analysis method proposed by Perkins, J. M. and Jinks, J. L. 1968. Heredity. 23: 339-359, Finlay, K. W. and Wilkinson, G. N. 1963. Aust. J. Res. 14: 742-754 and Eberhart, S. A. and Russell, W. A. 1966. Crop Sci. 6:36-40 to calculate the regression coefficient (b), S. E. and variance due to deviation from regression (S2d) as a parameter of stability and adaptability. The model described by Eberhart and Russell has the following formula:

$$P_{ij}=\mu+g_i+b_it_j+\delta_{ij}+e_{ij}$$

where $P_{ij}$ is the mean phenotype of genotype or cultivar i in location j,

μ is the grand mean across the whole experiment for all genotypes and locations, $g_i$ is the effect of genotype i across all locations $b_i$ is the linear regression of $P_{ij}$ on $t_j$, $t_j$ is the environmental index, that is the effect of environment j across all genotypes), $\delta_{ij}$ is the deviation $P_{ij}$ from the linear regression value for a given $t_j$ and $e_{ij}$ is the within environment error.

Categorization of Land Bases into Environmental Classes

Figure 5:
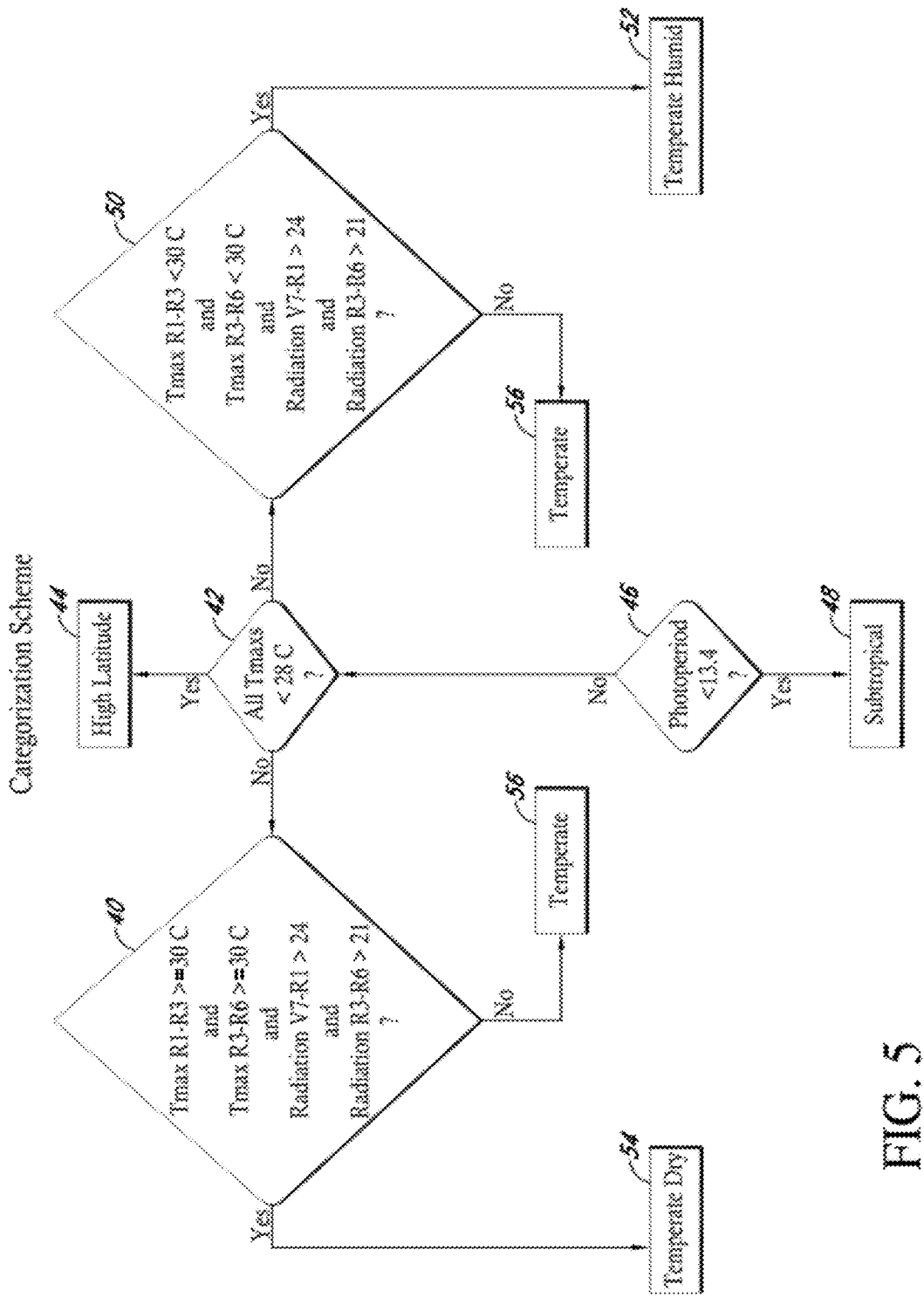
FIG. 5 illustrates one possible schematic for categorizing different land bases into environmental classifications based on temperatures, solar radiation, and length of photoperiod.

Using the information collected for or from G×E analysis, the land bases may be categorized into environmental classifications. FIG. 5 illustrates one possible schematic for categorizing different land bases into environmental classifications. With reference to FIG. 5, one method of categorizing environmental classifications is illustrated as a flow chart which provides environmental classifications based on temperature and/or high photo/sunlight. If all maximum temperatures are greater than 28° Celsius 42, then the land base may be categorized as either Temperate Dry 54, Temperate Humid 52, Temperate 56, or Subtropical 48. If all maximum temperatures are greater to or equal to 30° Celsius and solar radiation is greater than 24 and 21 at a given crop development stage, e.g. v7-R1, R3-R6 40, then the land base is characterized as Temperate Dry 54. If the maximum temperature is not greater than or equal to 30° Celsius and solar radiation is not greater than 24 at a given crop development stage, e.g. V7-R1 and 21 for R3-R6 respectively 40, then the land base is characterized as Temperate 56. However, if the maximum temperature is less than 30° Celsius and solar radiation is greater than 24 and 21 at a given crop development stage 50, then the land base is characterized as Temperate Humid 52. If the maximum temperature is not less than 30° Celsius and solar radiation is not greater than 24 and 21 at a given crop development stage 50, then the land base is characterized as Temperate 56. If all maximum temperatures 42 for the land base are less then 28° Celsius than the land base is characterized as High Latitude 44. In contrast, if all maximum temperatures 42 for the land base are not less then 28° Celsius and the land base has a photoperiod less than 13.4 hours/day 46, then the land base is Subtropical 48.

Figure 6:
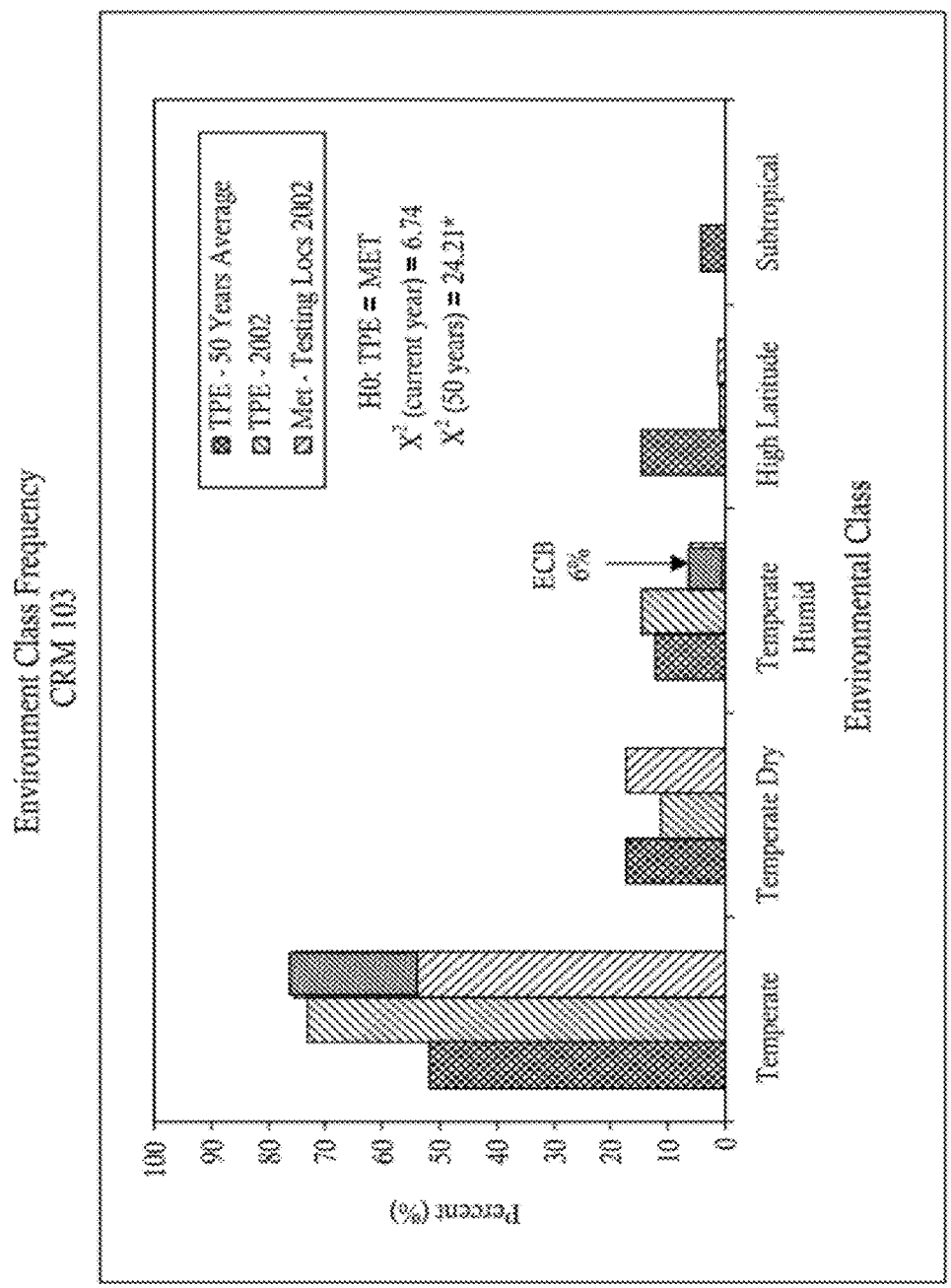
FIG. 6 is a bar graph representation of the frequency of various environmental classes among target population of environments (TPEs) or multi-environment trials (METs).
Figure 7:
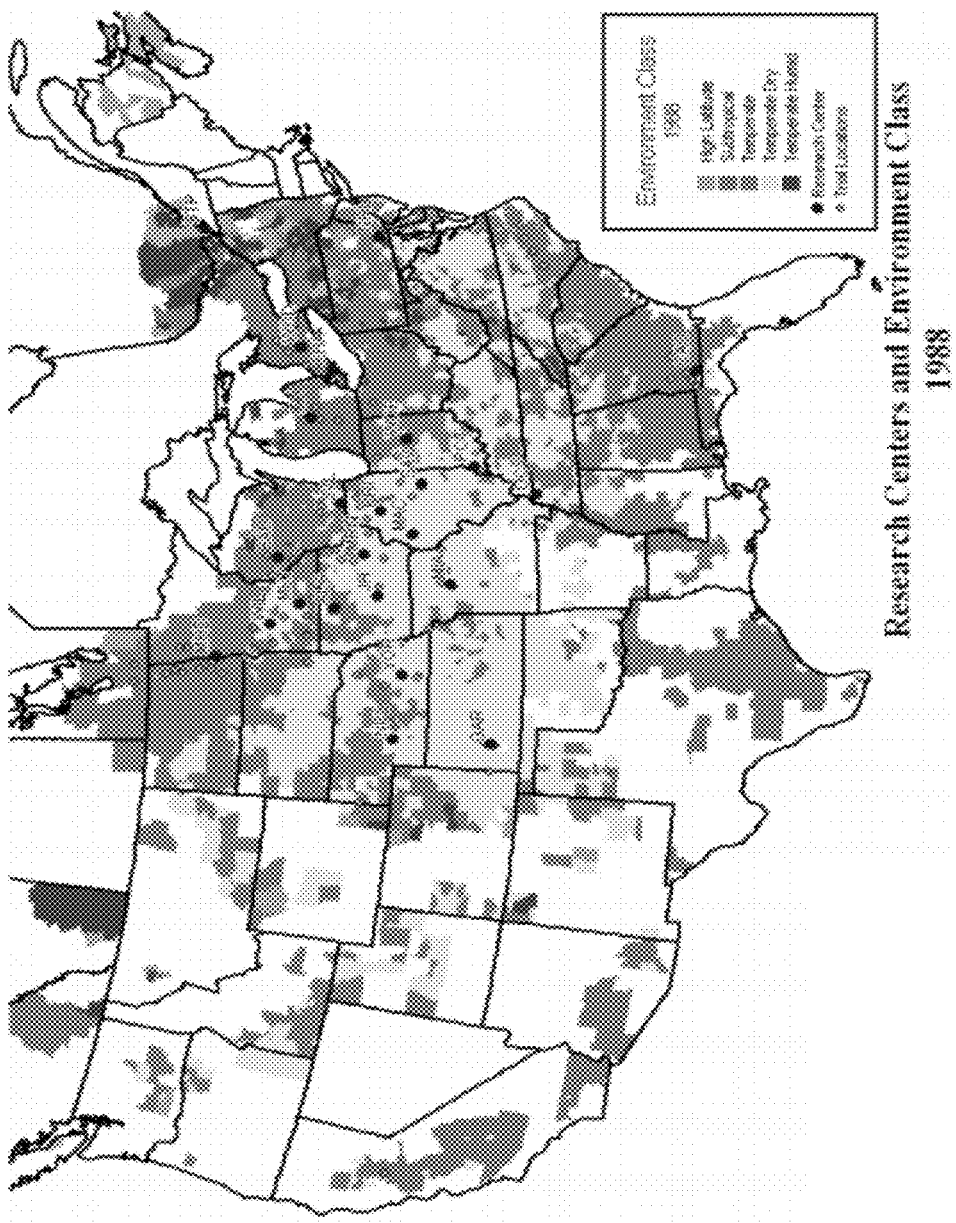
FIG. 7 illustrates potential categories of environmental classes identified throughout the United States in 1988 and their locations; these include temperate, temperate dry, temperate humid, high latitude, and subtropical classes.

Categorizing land bases into environmental classifications has several advantages. First, environmental classifications can bring an understanding of the various environments under which crops are produced. Second, occurrence probabilities for each environmental category can be assigned to each geographic location and the frequency of the classifications determined using routine methods. FIG. 6 is a bar graph representation of the frequency of various environmental classes among TPEs or METs. The frequency for each environmental class, e.g. temperate, temperate dry, temperte humid, high latitude, and subtropical, is given as a percent of the total TPE or MET tested in given year or across years. FIG. 7 illustrates potential categories of environmental classes identified throughout the United States in 1988 and their locations; these include temperate, temperate dry, temperate humid, high latitude, and subtropical classes. It will be apparent to one skilled in the art that other environmental classifications may added as identified or deemed relevant to G×E interactions for various crops.

Some of the environmental classification may be defined using general characteristics of climates. For example, temperate may be used to refer to regions in which the climate undergoes seasonal change in temperature and moisture; typically these regions lie between the Tropic of Capricorn and Antarctic circle in the Southern Hemisphere and between the Tropic of Capricorn and the Arctic circle in the Northern Hemisphere. Temperate humid may refer to regions in which the climate undergoes seasonal change in temperature and moisture and has more humidity than a temperate environment. High latitude as an environmental class may refer to regions that have a longer photoperiod than and is typically north of a particular latitude. A subtropical class may refer to regions enjoying four distinct seasons usually with hot tropical summers and non-tropical winters with a shorter photoperiod/day length; typically these regions lie between the ranges 23.5-40° N and 23.5-40° S latitude. The environmental classes may also be defined by biotic factors, such as diseases, insects, and/or characteristic of a plant. For example, an ECB class may refer to regions having European Corn Borers (ECB) or the suspected presence of ECB as evidenced by preflowering leaf feeding, tunneling in the plant's stalk, post flowering degree of stalk breakage and/or other evidence of feeding. The environmental class Brittle may be used to refers to regions where stalk breakage of corn occurs or is apt to occur near the time of pollination and is indicative of whether a hybrid or inbred would snap or break near the time of flowering under severe winds.

It is to be understood that the environmental classifications may be used and defined differently for different crops/genotypes and that these definitions may vary from year to year, even for the same crops or genotypes. For example, in 2000-2003, trials conducted studying G×E interactions among Comparative Relative Maturity (CRM) hybrids of CRM 103-113 in different environments identified seven different environmental classes—temperate, temperate dry, temperate humid, high latitude, subtropical, ECB, and brittle. For the study purposes, temperate was identified/defined as having a low level of abiotic stresses, a growing season adequate for CRM 103-113, and found to be frequent in Iowa and Illinois. Temperate dry was defined as temperate with high sunlight interception/intensity found to be frequent in Nebraska, Kansas, and South Dakota. Temperate Humid was defined as similar to the temperate environmental class but had a complex of biotic factors, such as leaf disease, that may differentially affect product performance. Temperate humid was also characterized as having a temperature and solar radiation lower than that identified in the temperate environmental class and found to be frequent in Indiana, Ohio, and Pennsylvania. The High Latitude environmental class was found to grow corn CRM 103 and earlier (growing hybrids) and experienced colder temperatures than the Temperate environmental class but with longer day-length. This environmental class was found to be frequent in Canada, North Dakota, Minnesota, Michigan, and Wisconsin. The fifth environmental class, Subtropical, was characterized as warm and humid with a short day-length and found frequently in the Deep South of the United States. Another environmental class identified was European Corn Borers (ECB) and defined as having *Bacillus thuringiensis* (Bt) hybrids that outyielded base genetics by at least 10%. The last environmental class Brittle defined areas with significant brittle damage with differential effect on products.

Once areas of land are categorized as environmental classes, these areas may be used in METs. Ultimately, the observed genotype performances in METs can be linked by the environmental class to the TPE. By evaluating product performance in a target environment, rather than merely performance differences in METs, genotype performance data from multiple test environments can be correlated to a target environment and used to predict product performance. This correlation between a genotype's performance and the target environment or environmental classification will lead to more precise product placement since the genotype performance is characterized within an environmental class in which it is adapted and most likely to experience after commercialization, consequently resulting in improved and more predictable product performance. The analysis of G×E interactions facilitates the selection and adoption of genotypes that have positive interactions with its location and its prevailing environmental conditions (exploitation of areas of specific adaption). G×E analysis also aids in the identification of genotypes with low frequency of poor yield or other performance issues in certain environments. Therefore, G×E analysis will help in understanding the type and size of G×E interactions expected in a given region. The present inventors contemplate that proper selection of hybrids for a particular land base will improve agricultural potential of certain geographic areas by maximizing the occurrence of crop performance through the use of the environmental classification. In addition, this approach allows the use of statistical and probability based analysis to quantify the risk of product success/failure according to the frequency of environment classes and the relative performance of genotypes within each environment class. This early identification and selection of hybrids would enable seed producers to start seed production and accelerate the development of hybrids in winter nurseries in warmer southern climates.

Moreover, environmental classification allows for the creation of an environmental profile for all or any part of the land base classified. Environmental classifications can be determined for each producer's land base. Similarly, the environmental performance profile of cultivars/hybrids can be determined through field experimentation or predicted using G×E analysis. In combining environmental classification frequencies for a particular land base and product performance by environmental classification, performance measurements are given the appropriate amount of relevance or weight for the land base in question. For example, the data are weighted based on long-term frequencies to compute a prediction of hybrid performance.

Use of G×E in Producer's Selection

According to another aspect of the present invention, a method of using information that documents the environmental profile over time of a crop producer's land base, the environmental performance profile of crop cultivars, and the producer's objectives to select a portfolio of cultivars that maximizes and quantifies the probability that the producer's objectives for productivity will be met. Environmental classification can be used to assist in this process.

Environmental classification can be used to determine the primary environmental drivers of G×E interaction in crops such as corn. That is, what are the primary environmental factors that cause change in the relative performance of hybrids. With this knowledge, crop production areas can be categorized into environmental frequency classes. Within these classes, hybrids tend to perform (as measured by yield, quality, or other performance data) relatively similar to one another. Across these classes, the relative performance of hybrids tends to be significantly different. Using historical meteorological information along with soils, pests, and other agronomic information, the frequency of these environments can be determined. This allows the creation of an environmental profile for all or any part of the geography classified. That is, a frequency distribution of the occurrence of the key Environment Classes. This can be done for each crop producer's land base.

Similarly, the environmental performance profile of crop cultivars can be determined through field experimentation. That is, a description of relative performance of cultivars can be determined in each of the key environment classes. In combining Environment class frequencies for a particular land area and product performance by Environment Class, performance measurements are given an appropriate amount of relevance or weight for the land area in question Thus, this aspect of the invention involves combining of this information at the producer's level to optimize crop productivity in such a way that it maximizes the probability of the producer's business operation reaching its productivity goals. The present invention contemplates that information can be used from any number of classification schemes to the selection of cultivars with the objective of maximizing the probability of attainment of the productivity and business goals of a crop producer's operation.

The approach of this aspect of the present invention does so by using compiled long term geo-referenced weather, soils, and agronomic data including biotic factors for the producer's land base to categorize the land base in terms of how frequently annual environmental variation occurs to a degree that is likely to impact relative hybrid performance. In addition, it can incorporate the producer's business objectives including, but not limited to preparedness to take risk. The present invention is able to combine environmental variability with producer business information to create a producer profile. Product performance information stratified by the same criteria is used to define the producer's environmental profile (for example, environmental classes) which is then integrated with the producer's profile.

The relative hybrid performance information that is relevant to the producer's land base is used regardless of when and where it was generated. The present inventors are first to predict future performance of genotypes and quantify probability/risk associated with that performance using data from environments that are considered to be substantially equivalent in terms of relative hybrid response. The result is a more robust and predictive data set thus allowing more informed product selection decisions that, over time will result in a higher probability of a producer operation meeting business objectives for productivity.

Figure 8:
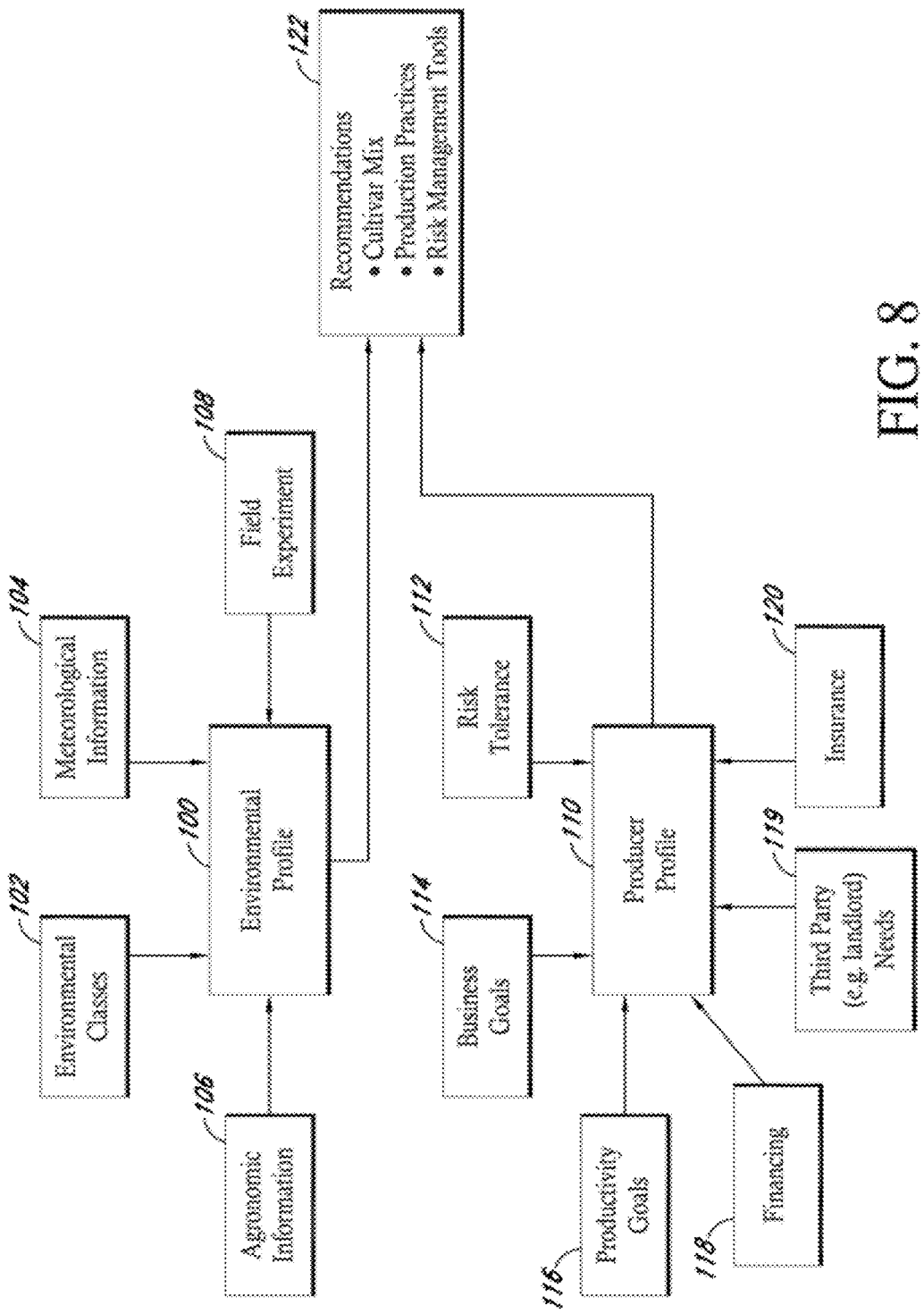
FIG. 8 is a flow diagram illustrating information flow from an environmental profile and a producer profile to providing recommendations to a producer according to one embodiment of the present invention.

FIG. 8 illustrates information flow according to one embodiment of the present invention. In FIG. 8 there is an environmental profile 100. The environmental profile can be based on one or more inputs such as environment classes 102, meteorological information 104, agronomic information 106, or field experimentation 108. In FIG. 1 there is also a producer profile 110. The producer profile 110 is based on one or more inputs such as risk tolerance 112 of the producer, business goals 114 of the producer, productivity goals 116, financing 118 considerations, third party needs 119, for example a landlord, or insurance/risk management and marketing 120 considerations. The environmental profile 100 and the producer profile 110 are combined in order to produce recommendations 122. The recommendations 122 can include risk management tools, a recommended seed product, a recommended mix of seed products, production practice recommendations, such as chemical application information, or any number of other specific recommendations as may be appropriate based on the particular environmental profile 100 and producer profile 110.

Figure 9:
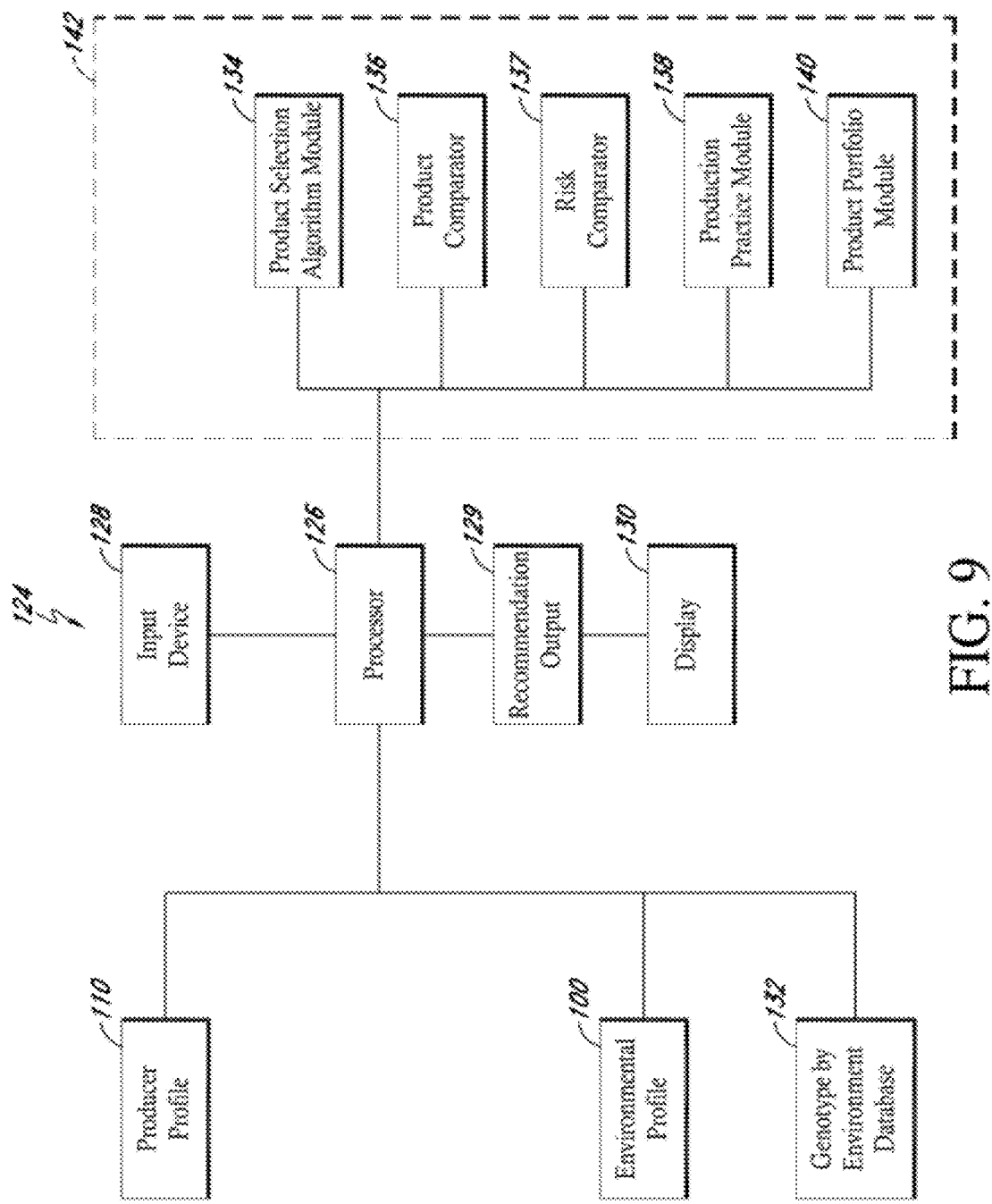
FIG. 9 is block diagram illustrating a system for determining product recommendations according to one embodiment of the present invention.

FIG. 9 illustrates one embodiment of a system 124 for producing product recommendations. In FIG. 9, a processor 126 accesses information associated with a producer profile 110, an environmental profile 100, and a genotype by environment database 132. There is an input device 128, a recommendation output 129, a records output 131, and a display 130 operatively connected to the processor. The records output 131 may be to maintain a record for the producer. The present invention contemplates that the processor 126 can be associated with a computer such as handheld computer as may be convenient for a dealer or sales agent. The present invention also contemplates that the producer profile 110, environmental profile 100, and genotype by environment database 132 may be accessible over a network, including a wide-area network such as the Internet.

Using the information in the producer profile 110, environmental profile 100, and genotype-by-environment database 132, the processor applies one or more of a product selection algorithm module 134, a product comparator 136, a production practice module and a risk comparator 138, and a product portfolio module 140. These and/or other modules are collectively the recommendation logic 142. In a simple case, the product selection algorithm module 134 would take information from the environmental profile 100, such as an environmental classification ("Temperate", for example) in addition to information from the producer profile 110, such as a producer objective ("Maximize Yield", "Risk Minimization", "Low Harvest Moisture" for example) and match these criteria to products in the genotype-by-environment database 132. Of course, more specific criteria could be examined as would be the case with more complex environmental profile information and more complex producer profile information.

Figure 10:
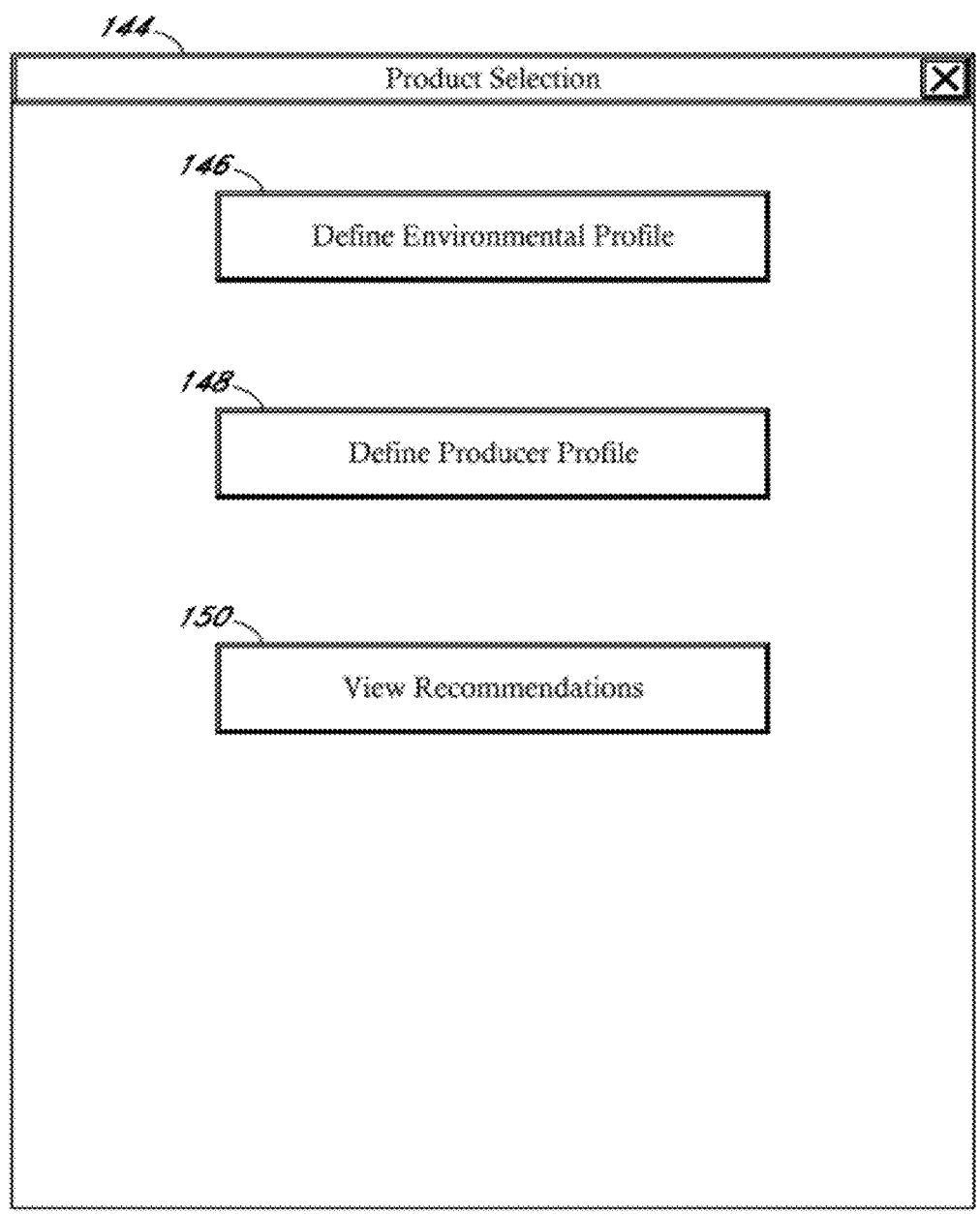
FIG. 10 is a screen display according to one embodiment of the present invention.

FIG. 10 illustrates one embodiment of a screen display 144 of a software application the present invention. In FIG. 10, a user is given the choice of selecting "DEFINE ENVIRONMENTAL PROFILE" 146, "DEFINE PRODUCER PROFILE" 148, and "VIEW RECOMMENDATIONS" 150. Of course, the present invention contemplates that software and its accompanying user interface can be implemented in any number of ways.

FIG. 11 illustrates one embodiment of a screen display 152 of a software application of the present invention. In FIG. 11, a recommendation is given which includes a plurality of products 154, an associated number of acres 156 associated with each of the products, a risk/probability assessment 157, and a recommended crop revenue assurance 158. The present invention provides for decreasing the amount of risk associated with selection of a particular seed product by instead selecting multiple products with different G×E interactions in order to reduce risk associated with environmental variations. The resulting selection, is somewhat akin to selection of stocks in a stock portfolio.

FIG. 12 and FIG. 13 illustrate embodiments of user interfaces to use in precision farming applications. In FIG. 12, the user interface 170 includes site-specific information associated with location information 172. The present invention contemplates that other site-specific information or historical information is accessible based on the location information 172 and may be used in product selections. In addition, environment and production information is collected. Examples of such information includes maturity days 176, input traits 178, output traits 180, seed treatment 182, tillage practices 174 used, the planting population 184, nitrogen utilization 186, and drought impact based on environmental classification drought frequency information 187 and soil type. In addition, field attribute information 185, such as, but not limited to crop history, soils, or other information, may be used. In addition, other types of production records associated with a particular location may be used. Based on this information and information associated with the location 172, a recommendation 188 of at least one hybrid seed product is made. Where multiple recommendations are made, the recommendations can be ranked as well as a risk assessment 189 such as shown.

FIG. 13 illustrates another embodiment of a user interface 200 that can be used in crop production applications. Site specific information is collected such as location 172, soil type 174, and number of acres 202. In addition, there is the option to import precision farming data 204 as well as import environment of frequency data 205. There are also the options to set production practices, set environmental assumptions, set risk levels, and set the maximum number of hybrids 212. Based on the inputs, a portfolio is created that includes a plurality of products 214, an associated number of acres 216 to plant for each product, a recommendation 217 of at least one hybrid seed product, a risk assessment 218, and revenue or crop insurance 219. Where multiple recommendations are made, the recommendations can be ranked. There is also an option to generate precision farming information 220 based on this information, such as a prescription map. The present invention contemplates that the precision farming information may indicate which acres to plant with which hybrids, give specific production practice application (such as chemical application rates), or other recommendations.

Figure 14:
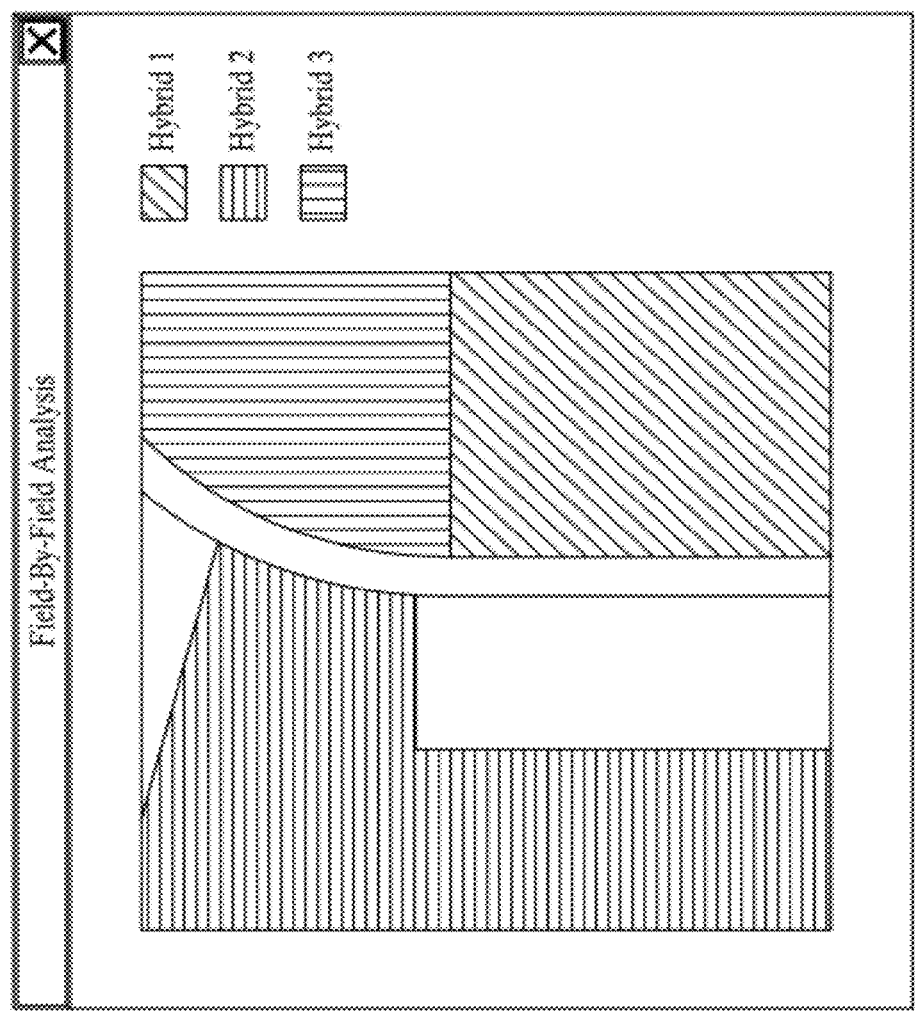
FIG. 14 is a screen display for one embodiment of the present invention showing field-by-field product recommendations.

FIG. 14 illustrates one example of a field-by-field analysis showing product recommendations for a land base of a producer. As shown in FIG. 14, different land areas within a producer's land base have different hybrids associated with them. The present invention contemplates producing such a map or field-by-field recommendations where multiple products are recommended. It should further be understood that a single producer or other user may have operations in a number of geographically diverse locations, and not necessarily the nearby fields illustrated in FIG. 14.

It should also be appreciated that the use of environmental classification and G×E interactions should be effectively communicated to customers. The effectiveness of the environmental classification process is based in part on its ability to use historical data from many locations so that all available data is used. This aspect of environmental classification would seem counter-intuitive to a customer who primarily relies upon personal knowledge in the local area. The customer's confidence in firsthand production knowledge can be used to assist in increasing confidence in environmental classification.

Figure 15:
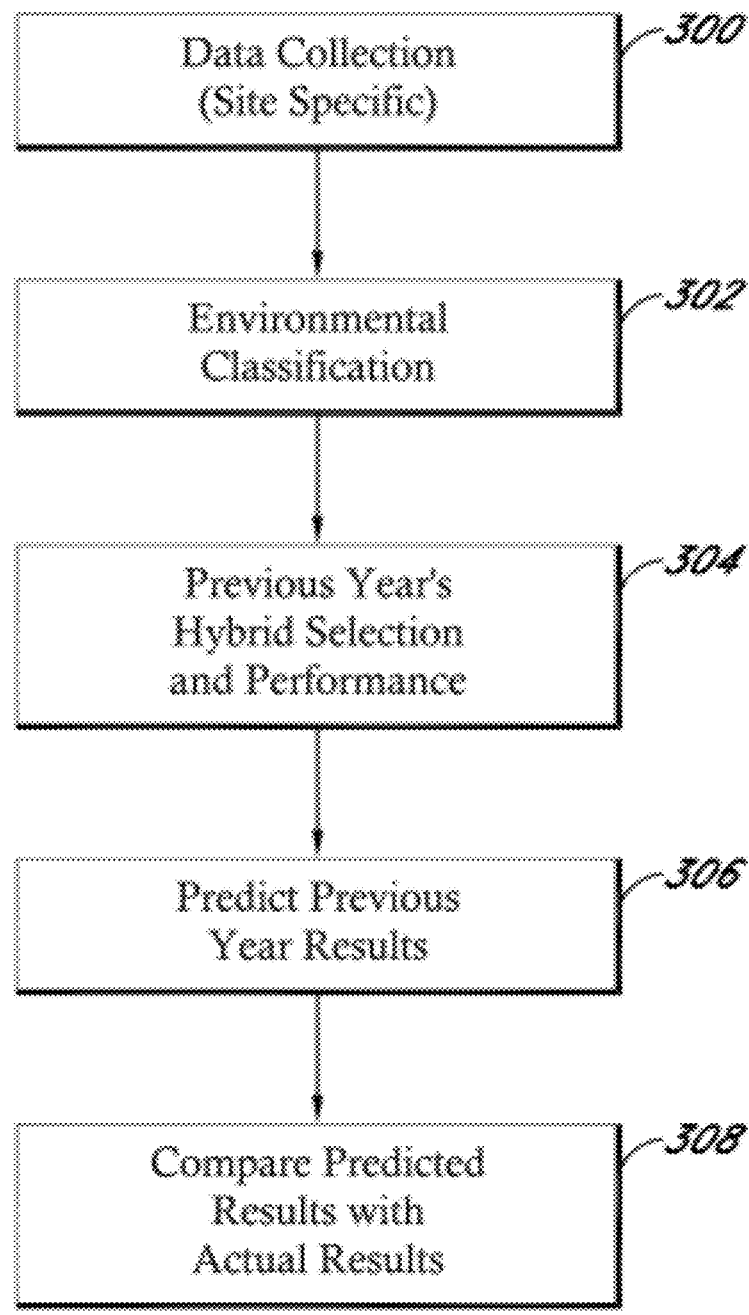
FIG. 15 is a flow diagram for one embodiment of a sales tool for demonstrating the value of environmental classification in describing relative performance.

FIG. 15 illustrates one example of the methodology of this aspect of the invention to assist in explaining these concepts to a producer. In step 300 site-specific data collection for a land base is performed. Based on this site-specific data collection, in step 302, the land base is given an environmental classification. In addition to this information, the type of hybrid selected in the previous year and its performance is provided by the producer in step 304. In step 306, a prediction is made as to the previous year's production based on environmental classification. In step 308, the predicted results are compared with the actual results. The present invention also contemplates not requiring performance results from the producer until after the previous year's results have been predicted in case the producer is not confident that an independent prediction is made.

Figure 16:
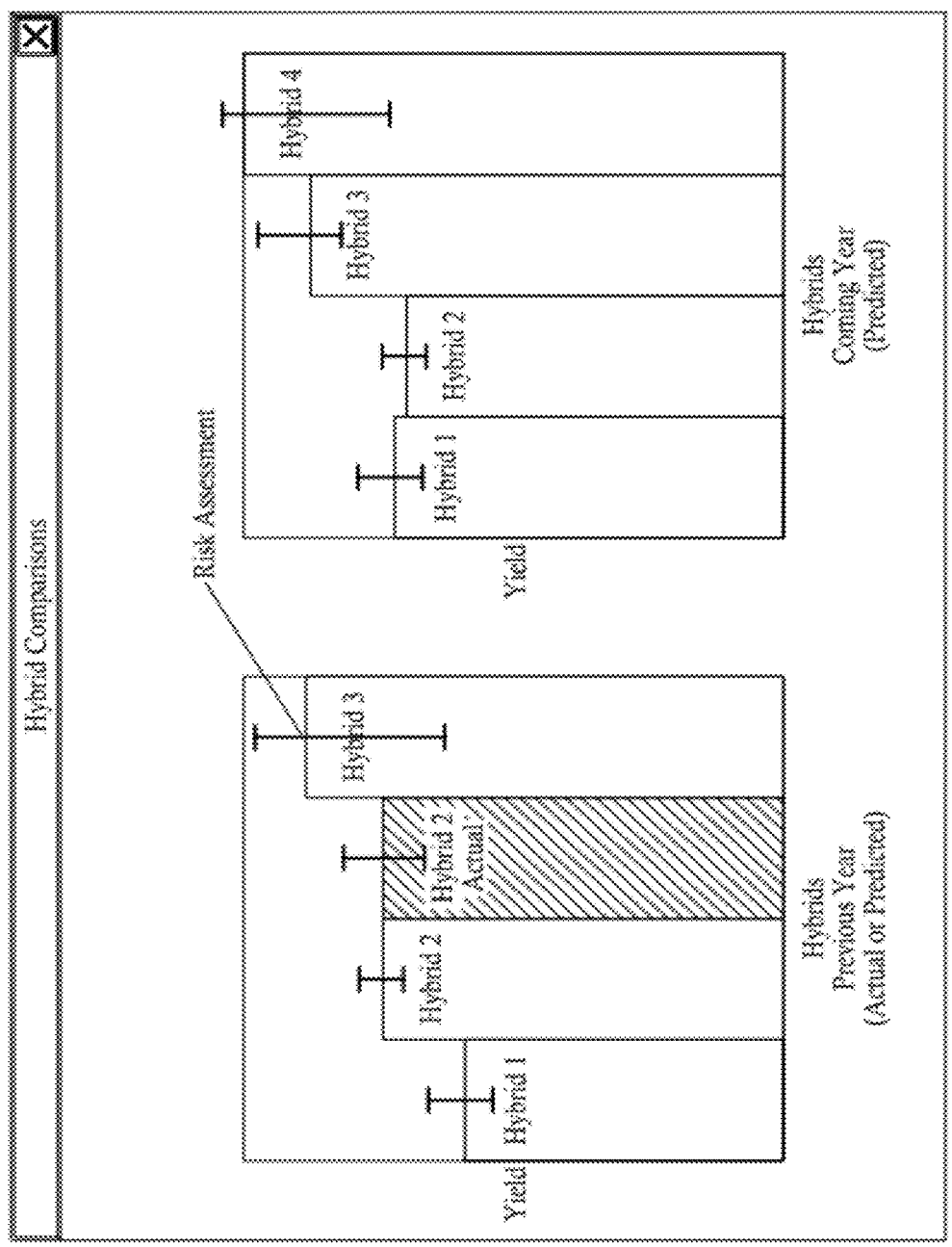
FIG. 16 is a screen display illustrating one example of output from a sales tool of the present invention for demonstrating the value of environmental classification in describing relative performance.
Figure 17:
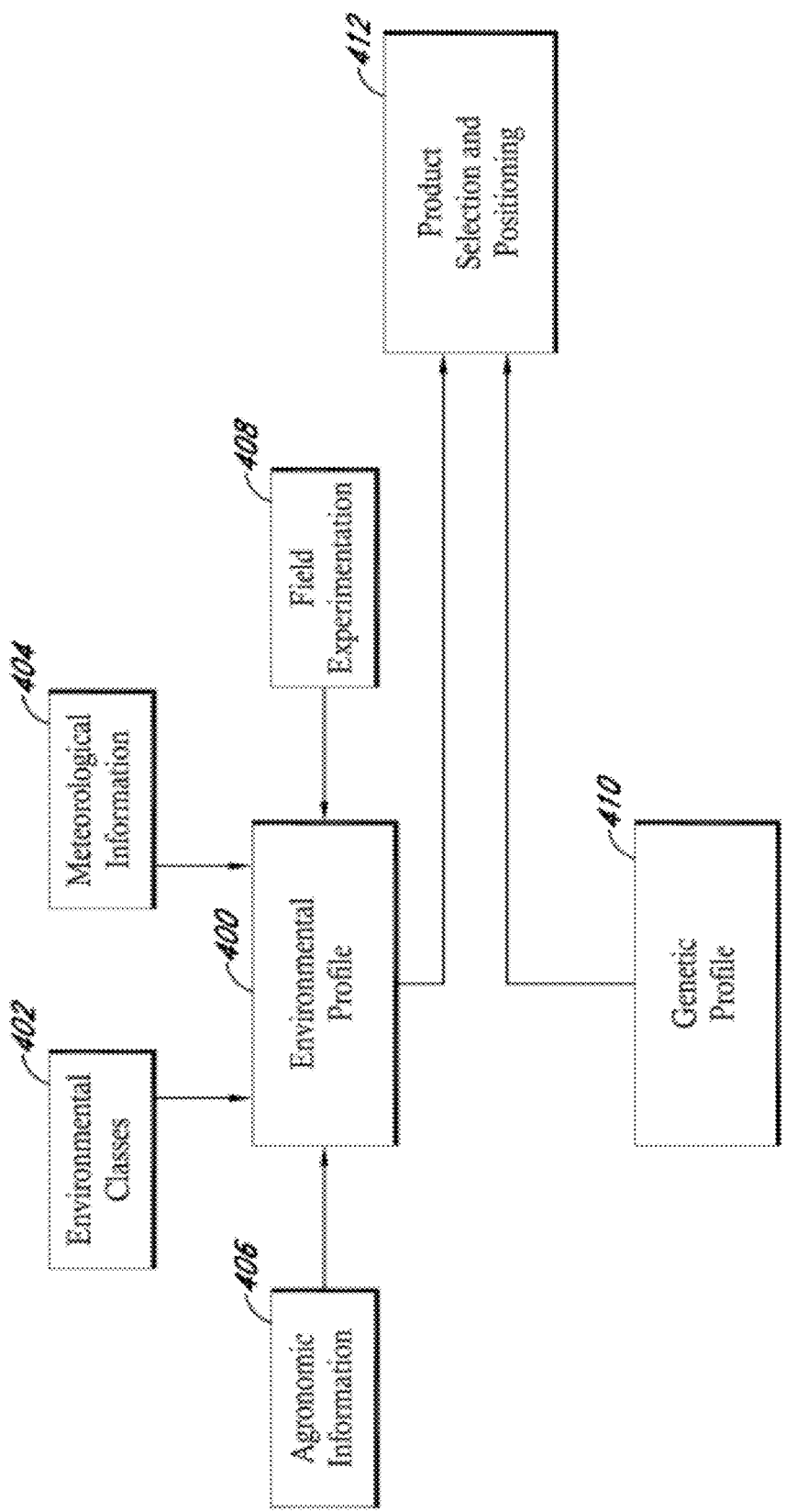
FIG. 17 is a flow diagram showing information flow in a product selection and positioning application of the present invention.

FIG. 16 illustrates one example of a screen display showing such comparisons. In FIG. 16, performance predictions (yield) are made for a number of different hybrids for both the previous year and the current year. In addition, a risk assessment for each hybrid may also be provided. The producer can compare the prediction for the previous year with the actual performance for that year in order to understand how well the environmental classification method can predict a result. If the producer is confident in the method's ability to correctly predict a result, the producer will be more inclined to use the prediction made for the coming year. The present invention contemplates that the same or similar information can be presented in any number of ways. It should further be understood that such a demonstration assists in illustrating the accuracy of the system in predicting relative performance differences between seed products. Due to the number of potential variables and difficulty in controlling such variables, accurate prediction of absolute performance is generally not a reasonable goal. However by selecting appropriate environmental classifications, useful insight into relative performance can be provided.

The present invention further recognizes the value of land base specific crop production records which include inputs, outputs, and parameters associated with environmental classification. The present invention provides a method to use such records as a part of the environmental classification system to improve analysis and recommendations. This includes, but is not limited to, risk assessment, input recommendations, recommendations for production practices.

Financial Incentives for Use of G×E and/or Environmental Classification

The present invention recognizes that agricultural input suppliers benefit from the success which they assist crop producers in obtaining. For example, when a seed product performs exceptionally well for a producer, such a seed product may be perceived as being of higher quality than competing products in future years. When a seed product performs poorly, such as seed product may be perceived as being of a lower quality or undesirable and the producer and other producers may be disinclined to purchase the seed product in future years. The same situation may apply for other types of inputs, including, but not limited to pesticides and fertilizers. It should be appreciated that these perceptions are not facts, but merely one data point. While the genotype for each of the products may be capable of producing high performers, the circumstances regarding the environment, and the resulting G×E interactions may have limited performance. Therefore, the result of the performance has very limited utility when viewed in isolation because the same or highly similar environmental conditions may not be present in the future years. The use of the environmental classification system of the present invention is advantageous as it incorporates significant data and therefore does not limit one to an isolated and restrictive view of the performance of an agricultural input.

As previously indicated, there may be some resistance to use of an environmental classification system by particular producers because it requires reliance on data that was not observed firsthand. Also, as previously indicated there is a benefit to suppliers of agricultural inputs to have producers provide the best results. To increase the likelihood of those results the present invention provides for promoting the use of environmental classification or other systems that take into account G×E interactions by providing a financial incentive to producers for doing so. The financial incentive can take on one or more of many different types. This can include a rebate on purchase price, financing for purchases at lower than normal rates such as prime or prime minus 1 percent financing. According to this methodology, a recommendation for a producer would be made using an environmental classification system. If the producer accepted the recommendation and made purchases based on the recommendation then the producer would receive the additional financial incentive. The recommendation may include the selection of one or more specific products, or may include a recommendation that one or more products be selected from a particular set of products. Such a methodology encourages the producer in making decisions based on G×E interactions and/or environmental classification.

Because environmental classification provides for managing risk, the present invention provides for others, instead of, and/or in addition to producers and input suppliers to benefit from this risk management. Generally, others with an interest in production management decisions include other stakeholders. Stakeholders can include banks or other financial institutions. Stakeholders could also include landlords, purchasers of resulting crops, or others. In one embodiment of the present invention, a bank or other financial institution requires or encourages a producer to use environmental classification for product selection and/or product positioning. For the previously indicated reasons, a producer may be reluctant to use environmental classification to manage risk. However, a bank or other financial institution providing financing desires to minimize risk. As a condition of financing, the bank or other financial institution may require the use of environmental classification.

In addition, a bank or other financial institution may use environmental classification for evaluating a producer's current or past selection of agricultural inputs. This is one manner in which a bank or financial institution may evaluate risk. Where a producer regularly makes poor selections of agricultural inputs, there may be greater risk associated with providing lending. Where such risks exist, a financial institution may decide to not lend money, or loan money under terms which better offset increased lending risks associated with the producer, such as higher interest rates. Where a producer has historically made poor decisions regarding agricultural inputs, a financial institution may also have additional incentive to require the producer to use the recommendations provided by an environmental classification system. Thus, the use of environmental classification also provides a method for evaluating past decisions of a producer in relationship to current decisions.

Figure 18:
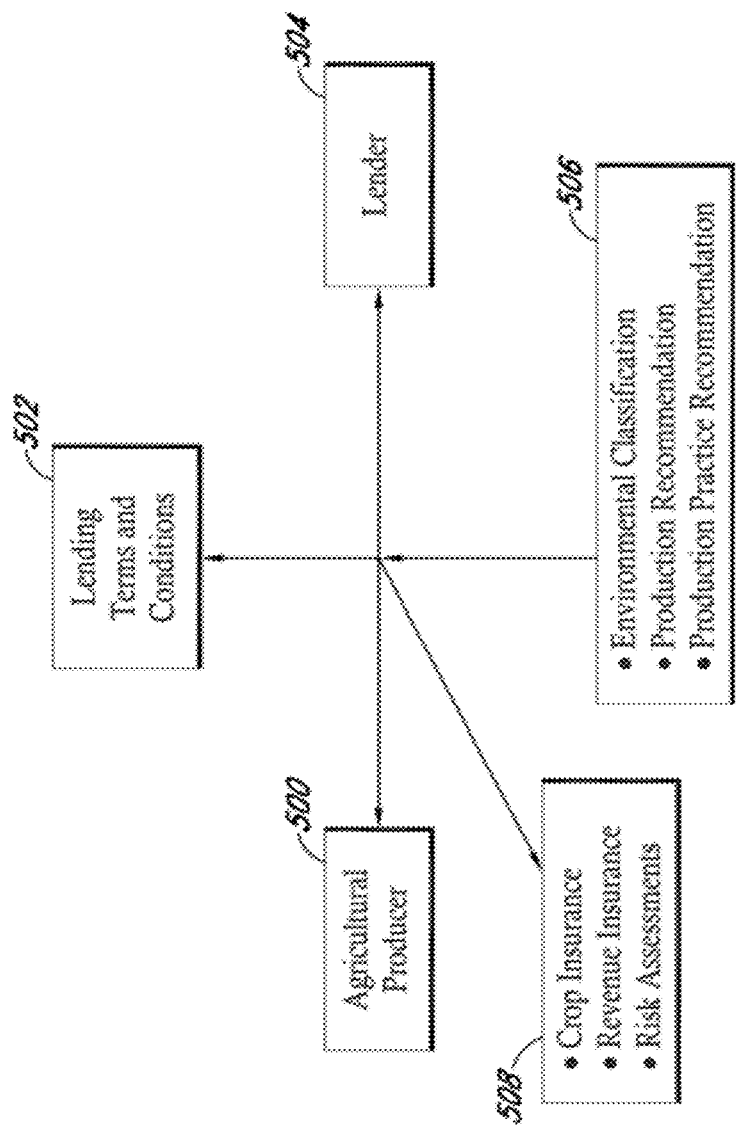
FIG. 18 is a block diagram illustrating financial and insurance interactions associated with agriculture production.

The methodology of the present invention can be applied to assisting in managing the risk associated with a loan transaction involving a producer and a lender. FIG. 18 provides an example of such a relationship. In FIG. 18, there is an agricultural producer 500 and a lender 504 with a relationship defined by lending terms and conditions 502. The present invention provides for using environmental classification, product recommendations, and production practice recommendations in determining the lending terms and conditions. The lending terms and conditions may include principal amounts, interest rates, and repayment terms. In addition the lending terms and conditions may have specific terms and conditions relating to environmental classification analysis, product recommendations based on environmental classification analysis, or production practice recommendations 506 based on environmental classification analysis. The use of descriptions of genotype-by-environment interactions, including environmental classification in association with risk assessments and a portfolio approach, enhances the ability of the lender to manage risk. Therefore, the lender may provide benefits or incentives to the agricultural producer who, for example, agrees to plant only those hybrids or other agricultural inputs appropriate for the environmental classification of the producer's land base. The benefit or incentive may be, without limitation, a reduced interest rate, a greater principal amount, or more favorable repayment terms. The lender may also require the use of approved hybrids appropriate for the environmental classification of the producer's land base. The lender might also require the use of risk management instruments, such as crop insurance or crop revenue insurance based on environmental classification of the land base and the recommendations and risk assessments 508 for seed products, herbicides, insecticides, and other inputs or production practices. Of course, the present invention contemplates combining this information with other information that may be used in determining whether or not to provide a loan and determining the lending terms and conditions. For example, production practice or production history information 503 may also be used. The present invention recognizes that genotype-by-environment interaction risks can be described and managed and that managing this risk, particularly at a producer level, allows for better managing of financial risks associated with crop production for all stakeholders.

Crop Insurance

The environmental classification methodologies of the present invention provide a statistically significant means to manage risk associated with genotype-by-environment interactions. The present invention provides for a number of methods and tools to assist in the management of risks and a number of products based on the increased understanding of risk and the predictive capabilities of these environmental classification methodologies.

One such aspect of the present invention relates to selection of a crop insurance plan. Although there are various software tools or other mechanisms available for selecting a crop insurance plan, the selection of a proper crop insurance plan is based on different scenarios of crop performance. One example of such a software tool is disclosed in U.S. Patent Publication No. 2005/0027572A1, herein incorporated by reference in its entirety. The present invention provides a means for determining more appropriate scenarios of crop performance which can then in turn be used to select an appropriate crop insurance plan. For example, environmental classification can be used to select preferred seed products as previously explained. The proper selection of seed products using environmental classification results in a statistical likelihood of better performance in a properly classified land base in a given year.

Although the present invention is not limited any specific types of crop insurance, specific examples of crop insurances are described herein. Examples of crop insurance include catastrophic coverage (CAT), Crop Revenue Coverage (CRC), Multi-Peril Crop Insurance (MPCI), and Revenue Assurance (RA).

In the United States, Catastrophic Coverage or CAT is the minimum level of MPCI coverage provided by FCIC. CAT insurance was created by Congress in 1994 to replace ad hoc disaster assistance—providing coverage for the equivalent of 27.5% of the value of the crop. Purchasing this minimum level of coverage allows producers to qualify for emergency disaster benefits and other farm support programs administered by local Farm Service Agencies. Farmers pay no premium, only a small administration fee per crop per county regardless of the type of crop or the number of acres. The policy reimburses lost bushels below the 50% yield guarantee at 55% of the established price.

Crop Revenue Coverage (CRC) provides coverage against the same perils as MPCI with the addition of upward and downward commodity market price movement. CRC protects against lost revenue caused by low prices, low yields or any combination of the two. The policy sets a market-based revenue guarantee in the spring before planting which is compared to calculated revenue raised using harvest price averages.

CRC insurance typically places a floor under yield and price risk, guaranteeing the policyholder will have inventory available or have it replaced at cash value. This allows producers to utilize various commodity marketing tools on guaranteed bushels at little to no risk. When harvest markets increase, so does the policy liability but at no additional premium charge.

The present invention provides for incorporating environmental classification information into the policy formation process. In particular, predicted yields based on environmental classification are used to set the market-based revenue guarantee in the spring. The present invention contemplates providing incentives to crop producers to use environmental classification. One example of such an incentive is to provide an increased revenue guarantee when the selection of seed products or other inputs or production management techniques are selected using environmental classification methodology. Another example of an incentive is to reduce premiums when product selections or other production management decisions are made according to recommendations based on environmental classification. Reducing the premium of a crop insurance policy is another example of providing a financial incentive to a producer for using environmental classification.

Income Protection (IP) is a revenue product that protects against reductions in gross income when yields or prices fall. In Income Protection insurance a revenue guarantee is set prior to planting and does not move. Indemnities are paid when actual revenue raised falls below the revenue guarantee. If fall market prices increase, revenue guarantee does not move and indemnities are less likely. The present invention provides for incorporating environmental classification methodologies with income protection insurance. The revenue guarantee may be set at least partially based on whether or not the insured uses environmental classification methodologies, or a particular product or service which uses environmental classification in making crop production decisions such as type of seed product to use, mix of seed product to use, chemical usage, or other crop production decisions. Alternatively, there may be the incentive for lowered premiums where a producer incorporates environmental classification methodologies into their crop production decisions. These are additional examples of where financial incentives are provided to a producer for using environmental classification.

Multi-Peril Crop Insurance (MPCI) is a U.S. federally regulated and subsidized yield guarantee program that covers losses due to adverse weather, insects, wildlife, diseases, replanting, prevented planting, poor quality and even earthquakes and volcanic eruption. Qualifying claims reimburse lost bushels (below the established bushel per acre guarantee) at an elected price per bushel.

Bushel guarantees are determined from a straight average of a minimum of four building to a maximum of ten years of actual production history. Approved yield histories permanently attach to the legal descriptions and the social security number of those with ownership of the crop.

Coverage rates, factors and reporting deadlines are written on a county basis. Coverage can be tailored by choosing options such as level, price, unit structure and prevented planting benefits. In this type of policy, the present invention also provides for tying incentives to the use of environmental classification to understand and/or predict environment by genetics interactions.

Revenue Assurance (RA) provides coverage against the same perils as MPCI with the addition of downward price movement and the option to purchase additional protection for upward price movement. RA offers coverage levels of 65% to 85%. For basic and optional units 80% and 85% are only on crops and in counties where MPCI allows 80 or 85%. Such a policy uses the producer's own Actual Production History (APH) to establish guarantees on a unit basis. Prices are established in the same manner as CRC. In this type of policy, the present invention also provides for tying incentives to the use of environmental classification to understand and predict genotype-by-environment interactions. The incentives can include increased coverage levels, decreased premiums, or other incentives.

Figure 19:
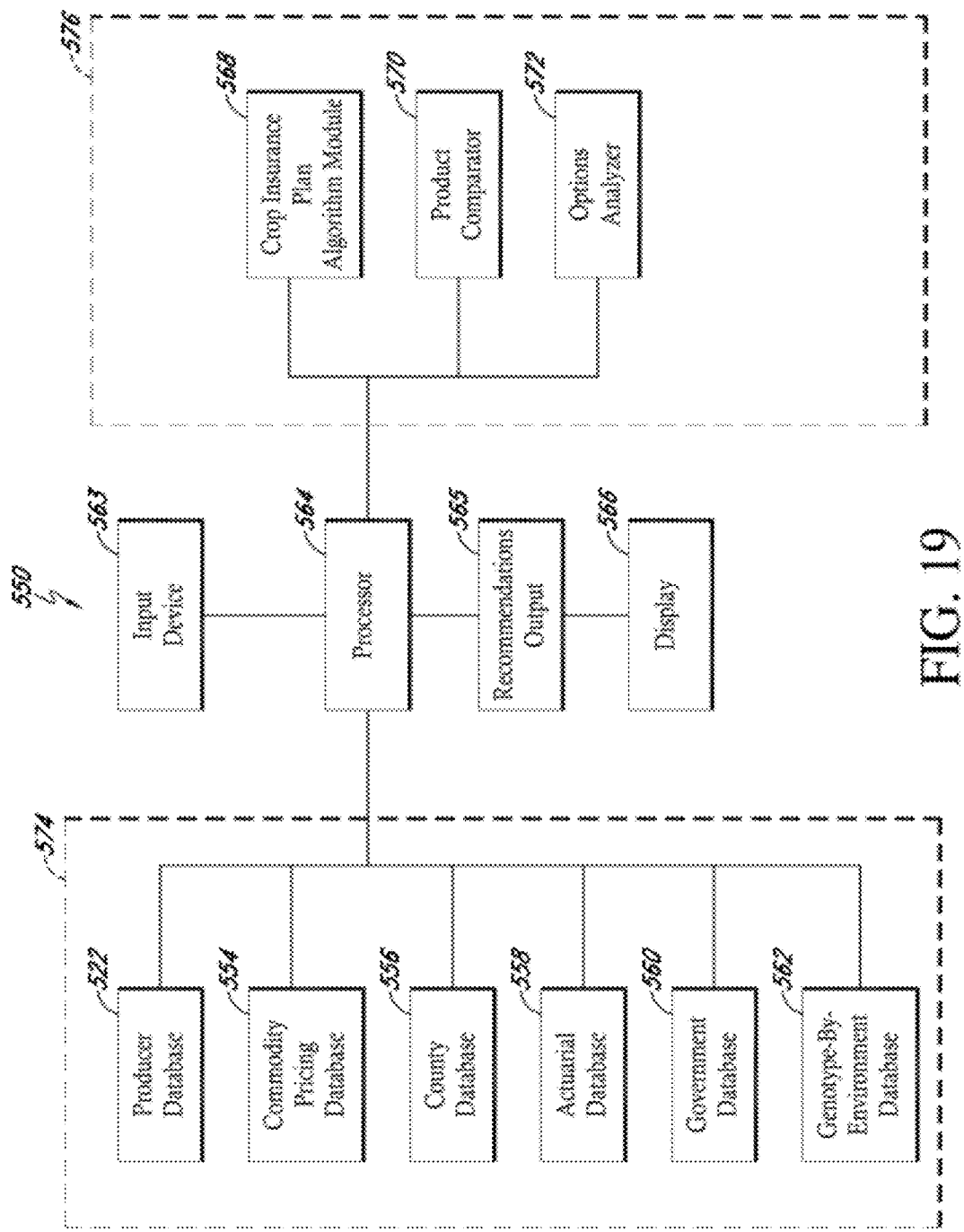
FIG. 19 is a block diagram illustrating one embodiment of a system of the present invention.

FIG. 19 illustrates one embodiment of the present invention where crop insurance is combined with environmental classification to assist in managing risk. In FIG. 19 a system 550 for making crop insurance recommendation is based in part on genotype-by-environment information, such as environmental classification information. In FIG. 19, inputs 574 include a producer database 552, a commodity pricing database 554, a county database 556, an actuarial database 558, a government database 560, a genotype-by-environment database 562, and an agronomic/production practices database 563. The databases may be accessed locally, or may be accessible over a network, such as a wide area network, or some combination thereof. The inputs 574 are operatively connected to a processor 564 which is operatively connected to input device 563, a recommendation output 565, a records output 567, and a display 566. The processor is programmed to run one or more crop insurance modules 576, including a crop insurance plan algorithm module 568, a product comparator module 570, and an options analyzer 572. The presence of the genotype-by-environment database 562 in the system allows for a statistically more accurate selection of a scenario of crop performance. Although there are various software tools or other mechanisms available for selecting a crop insurance plan, the selection of a proper crop insurance plan is based on different scenarios of crop performance. One example of such a software tool is disclosed in U.S. Patent Publication No. 2005/0027572A1, herein incorporated by reference in its entirety. The present invention provides a means for determining more appropriate scenarios of crop performance which can then in turn be used to select an appropriate crop insurance plan. For example, environmental classification can be used to select preferred seed products or other agricultural inputs as previously explained. The proper selection of seed products using environmental classification results in statistically greater production in a properly classified land base in a given year.

The proper use of environmental classification generally reduces the risk of the insurer which can result in increased revenue for the insurer and the potential for savings for the insured or incentives for the insured. The present invention also provides for individual underwriting which is generally considered to result in policies that are more fair to all parties involved.

The present invention contemplates numerous variations from the specific embodiments provided herein. These include variations in the environmental classifications, performance characteristics, software or hardware where used, the type of and other variations.

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

What is claimed:

1. A method for providing a crop insurance policy to a producer, the method comprising:
    receiving an evaluation, according to an environmental classification system, of use of agricultural inputs for a land base associated with a producer, wherein each of the agricultural inputs being associated with an environmental class according to the environmental classification system, and wherein the land base being associated with an environmental class according to the environmental classification system;
    determining a recommended agricultural input of the agricultural inputs, wherein the recommended agricultural input is based on the environmental class associated with each agricultural input and the environmental class associated with the land base;
    determining a production risk associated with using the recommended agricultural input at the land base; and
    determining, via a processor, one or more terms of the crop insurance policy based on the production risk associated with using the recommended agricultural input at the land base; and
    providing the crop insurance policy including the one or more terms to the producer.

2. The method of claim 1 wherein the environmental classification system is at least partially based on genotype by environment interactions.

3. The method of claim 1 wherein the crop insurance policy is a crop revenue insurance policy.

* * * * *